US010961352B2

(12) United States Patent
Nguyen et al.

(10) Patent No.: US 10,961,352 B2
(45) Date of Patent: Mar. 30, 2021

(54) CROSSLINKED AMINOSILICONE POLYMER AND METHODS FOR ITS PREPARATION AND USE

(71) Applicant: Dow Silicones Corporation, Midland, MI (US)

(72) Inventors: Kimmai Nguyen, Midland, MI (US); Qian Feng, Midland, MI (US); Nisaraporn Suthiwangcharoen, Midland, MI (US); Hannah Wedge, Midland, MI (US); Severine Cauvin, Seneffe (BE); Jonathan Thill, Seneffe (BE); Bethany Johnson, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 16/635,300

(22) PCT Filed: Oct. 30, 2018

(86) PCT No.: PCT/US2018/058072
§ 371 (c)(1),
(2) Date: Jan. 30, 2020

(87) PCT Pub. No.: WO2019/099180
PCT Pub. Date: May 23, 2019

(65) Prior Publication Data
US 2020/0369834 A1 Nov. 26, 2020

Related U.S. Application Data

(60) Provisional application No. 62/589,579, filed on Nov. 22, 2017, provisional application No. 62/588,538, filed on Nov. 20, 2017.

(51) Int. Cl.
| *C08G 77/18* | (2006.01) |
| *A61K 8/898* | (2006.01) |
| *A61Q 5/02* | (2006.01) |
| *A61Q 5/12* | (2006.01) |
| *C11D 3/00* | (2006.01) |
| *C11D 3/37* | (2006.01) |
| *C11D 11/00* | (2006.01) |
| *C11D 17/00* | (2006.01) |

(52) U.S. Cl.
CPC .............. *C08G 77/18* (2013.01); *A61K 8/898* (2013.01); *A61Q 5/02* (2013.01); *A61Q 5/12* (2013.01); *C11D 3/0015* (2013.01); *C11D 3/3742* (2013.01); *C11D 11/0017* (2013.01); *C11D 17/0017* (2013.01); *A61K 2800/48* (2013.01)

(58) Field of Classification Search
CPC .............. C11D 3/0015; C11D 17/0017; C11D 11/0017; C11D 3/374; A61Q 5/12; A61Q 5/02; A61K 8/898; A61K 2800/48; C08G 77/26; C08G 77/18; C08L 83/08; C08K 5/1515; C08K 5/5435
See application file for complete search history.

(56) References Cited

U.S. PATENT DOCUMENTS

| 2,798,053 | A | 7/1957 | Brown |
| 3,958,581 | A | 5/1976 | Abegg et al. |
| 3,962,418 | A | 6/1976 | Birkofer |
| 4,009,256 | A | 2/1977 | Nowak, Jr. et al. |
| 4,122,029 | A | 10/1978 | Gee et al. |
| 4,704,272 | A | 11/1987 | Oh et al. |
| 4,788,006 | A | 11/1988 | Bolich, Jr. et al. |
| 5,387,417 | A | 2/1995 | Rentsch |
| 5,543,074 | A | 8/1996 | Hague et al. |
| 5,811,487 | A | 9/1998 | Schulz, Jr. et al. |
| 5,852,110 | A | 12/1998 | Gee |
| 5,919,441 | A | 7/1999 | Mendolia et al. |
| 5,981,680 | A | 11/1999 | Petroff et al. |
| 6,013,682 | A | 1/2000 | Dalle et al. |
| 6,051,216 | A | 4/2000 | Barr et al. |
| 6,916,464 | B2 | 7/2005 | Hansenne et al. |
| 7,078,026 | B2 | 7/2006 | Ferrari et al. |
| 2003/0050393 | A1 | 3/2003 | Ferritto |
| 2003/0072730 | A1 | 4/2003 | Tournilhac |
| 2003/0170188 | A1 | 9/2003 | Ferrari |
| 2003/0235553 | A1 | 12/2003 | Lu et al. |
| 2004/0180032 | A1 | 9/2004 | Calello |
| 2004/0223936 | A1 | 11/2004 | Fecht |
| 2005/0272332 | A1* | 12/2005 | Carswell ........... D06M 15/3562 442/59 |
| 2010/0098648 | A1 | 4/2010 | Yu |
| 2014/0235885 | A1* | 8/2014 | Koczo ................ C08F 8/42 556/423 |
| 2017/0000722 | A1 | 1/2017 | Feng et al. |

FOREIGN PATENT DOCUMENTS

| DE | 10 2004025131 A1 * | 12/2004 |
| DE | 10 2004 025 131 | * 12/2005 |
| DE | 102004025131 | 12/2005 |
| EP | 266648 | 5/1988 |
| EP | 1266647 | 12/2002 |
| EP | 1266653 | 12/2002 |
| WO | 2003105789 | 12/2003 |
| WO | 2003105801 | 12/2003 |
| WO | 2003106614 | 12/2003 |
| WO | 2004000247 | 12/2003 |
| WO | 2004054523 | 7/2004 |
| WO | 2004054524 | 7/2004 |
| WO | 2004060101 | 7/2004 |

OTHER PUBLICATIONS

Machine Translation of Spitzner et al. (DE 10 2004 025 131 A1), 2005.*

* cited by examiner

Primary Examiner — Blessing M Fubara
(74) Attorney, Agent, or Firm — Catherine U. Brown

(57) ABSTRACT

A Crosslinked Aminosilicone Polymer is useful in personal care applications, particularly hair care or textile treatment. A process for making the Crosslinked Aminosilicone Polymer is also described.

20 Claims, No Drawings

CROSSLINKED AMINOSILICONE POLYMER AND METHODS FOR ITS PREPARATION AND USE

CROSS REFERENCE TO RELATED APPLICATIONS

This application is a U.S. national stage filing under 35 U.S.C. § 371 of PCT Application No. PCT/US18/058072 filed on 30 Oct. 2018, currently pending, which claims the benefits of both U.S. Provisional Patent Application No. 62/588,538 filed 20 Nov. 2017 and U.S. Provisional Patent Application No. 62/589,579 filed 22 Nov. 2017, under 35 U.S.C. § 119 (e). PCT Application No. PCT/US18/058072, U.S. Provisional Patent Application No. 62/588,538, and U.S. Provisional Patent Application No. 62/589,579 are hereby incorporated by reference.

TECHNICAL FIELD

A crosslinked aminosilicone polymer, methods of making the polymer, and use of the polymer for treating hair, textiles, other fibers, and other substrates are disclosed.

BACKGROUND

Silicones have been used extensively for hair, textile, and other fiber treatments. In particular, various amine functional silicones have been developed and sold commercially under various trade names. Common problems associated with amine functional silicones as textile treatments are their yellowing of textiles from the oxidation of the amine groups and extensive hydrophobic nature of the polydimethylsiloxane chains. Thus, efforts over the years have focused on modifying amine functional silicones by adding hydrophilic groups to the siloxane polymers, e.g., as silicone polyether block copolymers, while altering or reducing the amine content to reduce yellowing.

There are several shortcomings using amine functional silicone polyether copolymers. They may be expensive and/or time consuming to prepare. Their performance, particularly in hair care applications, may be insufficient. There is an industry need for cost effective functional silicone materials for hair care compositions that can provide conditioning and/or styling benefits to hair.

SUMMARY

This invention relates to a Crosslinked Aminosilicone Polymer. Said Crosslinked Aminosilicone Polymer comprises average unit formula:

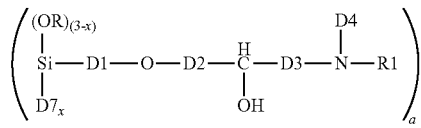

-continued

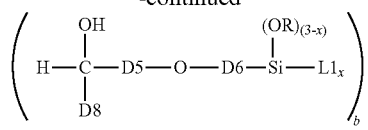

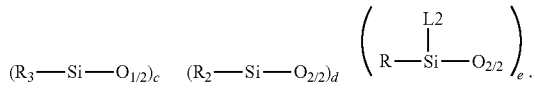

In the unit formula above, each R is independently a monovalent hydrocarbon group of 1 to 6 carbon atoms. Each L1 is a linking moiety. L1 bonds with D7. Each L2 is a linking moiety. L2 bonds with D4. D1 is a divalent hydrocarbon group of 2 or more carbon atoms. D2 is a divalent hydrocarbon group of 1 or more carbon atoms. D3 is a covalent bond or a divalent hydrocarbon group of 1 or more carbon atoms. D4 is a divalent hydrocarbon group of 2, more carbon atoms or an aminofunctional alkylene group of 2 or more carbon atoms, or a reaction product of NH and epoxy. Each R1 is independently a hydrogen atom or a covalent bond linking to D8. D5 is a divalent hydrocarbon group of 1 or more carbon atoms. D6 is a divalent hydrocarbon group of 2 or more carbon atoms. D7 is an oxygen atom. D8 is a covalent bond or a divalent hydrocarbon group of 1 or more carbon atoms. Each subscript x is independently 0, 1, or 2. Subscript a is 1 or more. Subscript b is 1 or more. Subscript c is 2 or more. Subscript d is 0 to 2000. Subscript e is 0 or more. A quantity (c+d+e) is up to 2000. The crosslinked aminosilicone has up to 10% amine content, alternatively up to 5% amine content).

This invention also provides a process for preparing the Crosslinked Aminosilicone Polymer comprising the average unit formula above by a process comprising emulsion polymerization of starting materials comprising (i) an organosilicone polymer having a hydroxyl group and/or an alkoxy group, (ii) an organosilicone polymer having a nitrogen containing monovalent hydrocarbon and a hydroxyl group, (iii) an organosilane having an alkoxy group and an epoxy-functional group, (iv) a surfactant, and (v) water.

This invention also provides a method of using the Crosslinked Aminosilicone Polymer with the formula above for treatment of substrates.

DETAILED DESCRIPTION

The Crosslinked Aminosilicone Polymer comprises the average unit formula:

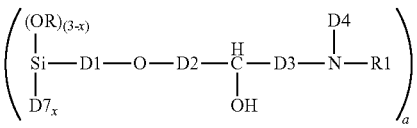

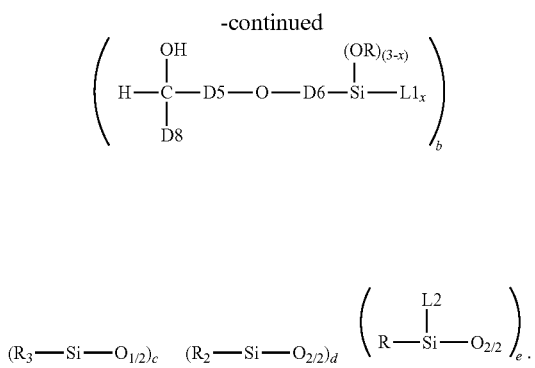

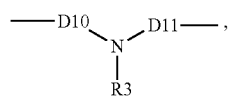

In the average unit formula above, each R is an independently selected monovalent hydrocarbon group of 1 to 6 carbon atoms. Suitable monovalent hydrocarbon groups for R include alkyl, alkenyl, alkynyl, and aryl, as defined below. Alternatively, each R may be alkyl, alkenyl, or aryl. Suitable alkyl groups are exemplified by methyl, ethyl, propyl (including branched and linear isomers, i.e., n-propyl and iso-propyl), butyl (including branched and linear isomers, i.e., tert-butyl, sec-butyl, iso-butyl, and n-butyl), and hexyl (including branched and linear isomers). Suitable alkenyl groups include vinyl, allyl and hexenyl. Suitable aryl groups include phenyl, tolyl, and xylyl, alternatively phenyl. Alternatively, each R may be selected from alkyl and aryl (e.g., methyl and phenyl). Alternatively, each R may be methyl.

Each L1 is an independently selected linking moiety. L1 bonds with D7. Each L2 is an independently selected linking moiety. L2 bonds with D4. Each L1 and each L2 may be a covalent bond.

D1 is a divalent hydrocarbon group of 2 or more carbon atoms. Alternatively, D1 may have 2 to 4 carbon atoms. D1 is exemplified by ethylene, propylene and butylene. Alternatively, D1 may be n-propylene.

D2 is a divalent hydrocarbon group of 1 or more carbon atoms. Alternatively, D2 may have 1 to 3 carbon atoms, e.g. methylene, ethylene and propylene.

D3 is a covalent bond or a divalent hydrocarbon group of 1 or more carbon atoms, as described above for D2. Alternatively, the divalent hydrocarbon group for D3 may have 1 to 2 carbon atoms, e.g., methylene or ethylene. Alternatively, D3 may be methylene.

D4 is a divalent hydrocarbon group of 2 or more carbon atoms or an aminofunctional alkylene group of 2 or more carbon atoms. Alternatively, the divalent hydrocarbon group for D4 may have 2 to 8 carbon atoms, alternatively 2 to 6 carbon atoms, and alternatively 2 to 4 carbon atoms. The aminofunctional alkylene group may have general formula:

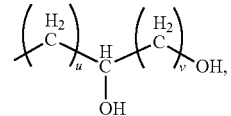

where D10 is an alkylene group of 1 to 6 carbon atoms, D11 is an alkylene group of 1 to 6 carbon atoms, and R3 is a hydrogen atom or group of formula:

$$\left(\begin{matrix}H_2\\C\end{matrix}\right)_u \begin{matrix}H\\C\\|\\OH\end{matrix} \left(\begin{matrix}H_2\\C\end{matrix}\right)_v OH,$$

where subscript u is 1 or more and subscript v is 1 or more. Alternatively, subscript u is 1 to 20 and subscript v is 1 to 20. Alternatively, subscript u is 1 to 10. Alternatively, subscript v is 1 to 10. Alternatively, a quantity (u+v) is 1 to 22. Suitable aminofunctional alkylene groups for D4 are exemplified by —$(CH_2)_2$—$N(R3)$—$(CH_2)_3$—, —$(CH_2)_2$—$N(R3)$—$(CH_2)_2$—, —$(CH_2)_3$—$N(R3)$—$(CH_2)_3$—, and —$(CH_2)CH(CH_3)$—$CH_2$—$N(R3)$—$(CH_2)_2$—, where R3 is as described above. Alternatively, D10 and D11 together may have a total of 3 to 8 carbon atoms, and alternatively 4 to 8 carbon atoms. Alternatively, D4 may be a group which is a reaction product of NH reacting with an epoxy functionality.

Each R1 is independently a hydrogen atom or a covalent bond linking to D8.

D5 is a divalent hydrocarbon group of 1 or more carbon atoms. Alternatively, D5 may have 1 to 3 carbon atoms, e.g. methylene, ethylene and propylene. Alternatively, D5 may be methylene or ethylene; alternatively methylene.

D6 is a divalent hydrocarbon group of 2 or more carbon atoms. Alternatively, D6 may have 2 to 4 carbon atoms. D1 is exemplified by ethylene, propylene and butylene. Alternatively, D6 may be n-propylene.

D7 is an oxygen atom when subscript x>0 and D7 is absent when x=0. Each subscript x is independently 0, 1, or 2.

D8 is a divalent hydrocarbon group of 1 or more carbon atoms (e.g., methylene).

Subscript a is 1 or more. Subscript b is 1 or more. Subscript c is 2 or more. Subscript d is 0 or more, alternatively subscript d is 0 to 2000. Subscript e is 0 or more. A quantity (c+d+e) is up to 2000. Alternatively, subscript a may be 1 to 100. Alternatively, subscript b may be 1 to 100. Alternatively, subscript c may be 2 to 100. Alternatively, subscripts a and b have values sufficient to provide an amine content to the Crosslinked Aminosilicone Polymer of >0 to 5 mole %, alternatively >0 to 2.5 mole %.

Subscripts a and b and group D4 are selected such that the Crosslinked Aminosilicone Polymer has >0 to 10 mole % amine content, alternatively >0 to 5 mole % amine content alternatively >0 to 2.5 mole %.

An exemplary Crosslinked Aminosilicone Polymer may have average formula:

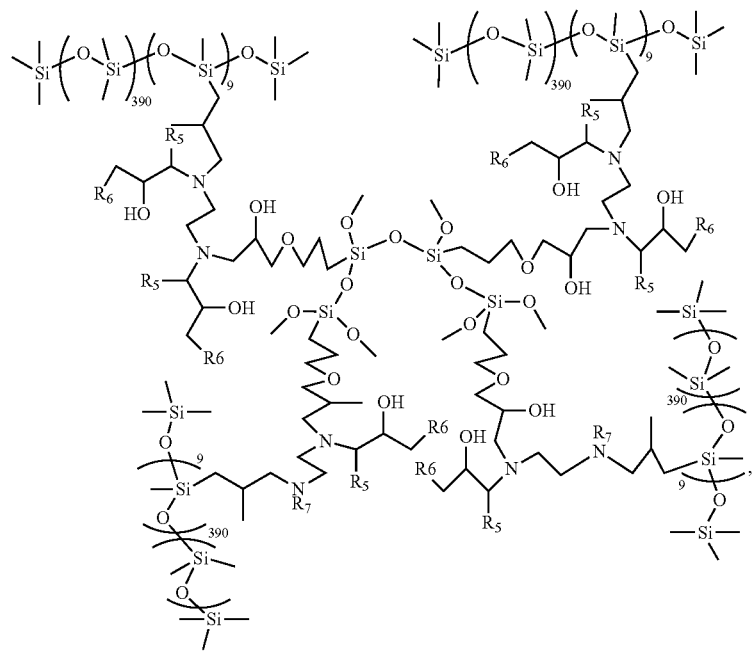
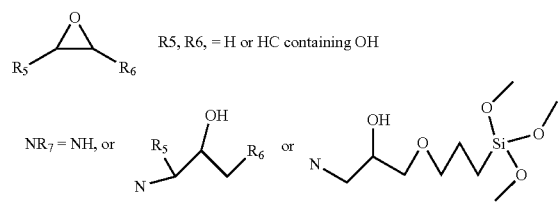
for example, when made by the process described below to make Emulsions A and B.
Alternatively, an exemplary Crosslinked Aminosilicone Polymer may have an average formula:
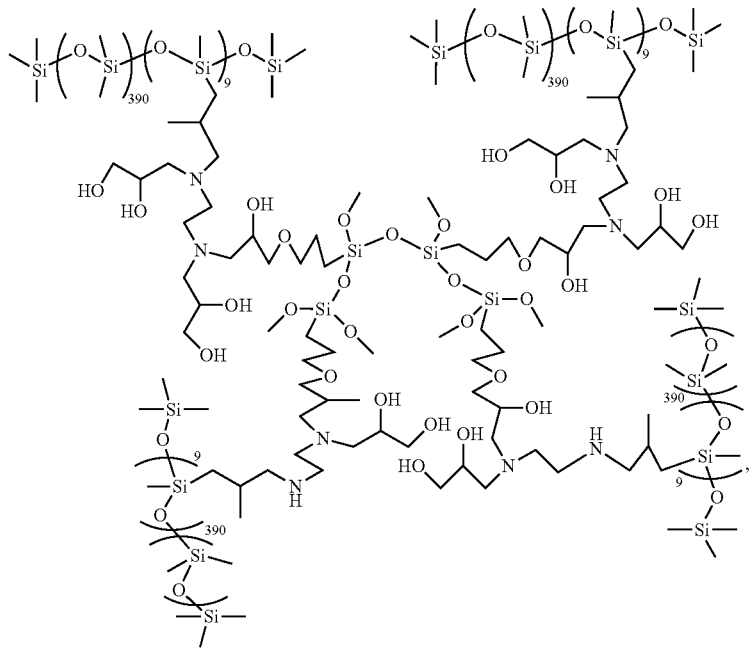

when glycidol is used in the process for preparing the Crosslinked Aminosilicone Polymer.

This invention further relates to processes for preparing the Crosslinked Aminosilicone Polymer described above. A process for preparing said Crosslinked Aminosilicone Polymer comprises: emulsion polymerization of starting materials comprising (i) an epoxy-functional organic compound, (ii) an organosilicone polymer having a nitrogen containing monovalent hydrocarbon and optionally a hydroxyl group, (iii) an organosilane having an alkoxy group and an epoxy-functional group, (iv) a surfactant, and (v) water.

The epoxy-functional organic compound has an oxirane group. Examples include glycidol methacrylate; n-butyl glycidyl ether; phenyl glycidol ether; 3,4-epoxy-1-cyclohexene; 9-OXABICYCLO[6.1.0]NON-2-ENE; 1-METHYL-7-OXABICYCLO[4.1.0]HEPT-3-ENE; metoprolol hydroxy epoxide; or 1,2-epoxy-9-decene. The epoxy functional organic compound may further comprise an alcohol functionality. Exemplary epoxy-functional organic compounds are commercially available and are exemplified by glycidol.

The organosilicone polymer having a nitrogen containing monovalent hydrocarbon and optionally a hydroxyl group used as starting material (ii) has the average formula: $(R_3SiO_{1/2})_c(R_2SiO_{2/2})_d(RR4SiO_{2/2})_e$, where R and subscripts c, d, and e are as described above and R4 is an aminofunctional group of formula:

where D12 is a divalent hydrocarbon group of 1 to 8 carbon atoms, alternatively 2 to 6 carbon atoms, alternatively 3 to 5 carbon atoms, and alternatively 4 carbon atoms. D13 is a divalent hydrocarbon group of at least 1 carbon atom, alternatively 1 to 8 carbon atoms, and alternatively 1 to 2 carbon atoms. The divalent hydrocarbon groups suitable for D12 and D13 are as described and exemplified herein. Alternatively, D12 and D13 may be alkylene groups, e.g., which may be independently selected from ethylene, propylene and butylene. Linear or branched alkylene groups may be used.

The organosilane having an alkoxy group and an epoxy-functional group used as starting material (iii) to make the Crosslinked Aminosilicone Polymer has the formula: $R^ESiR2_{(3-y)}(OR)_y$, where subscript y is 1 to 3, each R2 is independently a monovalent hydrocarbon group of 1 to 12 carbon atoms, and each $R^E$ is an epoxy-functional monovalent group. Examples of suitable organosilanes for starting material (iii) include, but are not limited to, epoxytrimethoxysilane, glycidoxypropyltrimethoxysilane, epoxytriethoxysilane, and glycidoxypropyltrimethoxysilane.

The surfactant and water used in the emulsion polymerization to prepare the Crosslinked Aminosilicone Polymer may be as described below. The emulsion polymerization may be performed by methods known in the art, such as that disclosed in U.S. Pat. No. 5,852,110 by substituting the starting materials described herein for those used in the reference. For example, emulsion polymerization may be performed by combining the surfactant and water, optionally with heating, and thereafter adding starting materials (i), (ii) and (iii) thereto, in any order. Alternatively, the method may comprise: 1) combining starting material (ii) the organosilicone polymer, (iv) the surfactant, and (v) a portion of the water, and thereafter 2) adding starting material (i) the epoxy-functional organic compound, and 3) adding starting material (iii) the epoxy-functional alkoxysilane. The remainder of the water may be added in step 2), step 3) or both. Alternatively, the method may comprise 1) combining starting material (ii) the organosilicone polymer, (iv) the surfactant and (v) a portion of the water, and thereafter 2) adding starting material (iii) the epoxy-functional alkoxysilane, and 3) adding starting material (i) the epoxy-functional organic compound. The remainder of the water may be added in step 2), step 3) or both. The resulting product, of the methods with different orders of addition as described above, is an emulsion containing a Crosslinked Aminosilicone Polymer as described above. The emulsion may be used as Treatment Composition described herein, or the Crosslinked Aminosilicone Polymer may be isolated from the emulsion using methods such as those described in U.S. Pat. No. 5,852,110.

Alternatively, any method described above may optionally further comprise adding a process aid, particularly if amino content of starting material (ii) is high. Suitable process aids are acids, such as the pH adjusting acids defined herein below.

Emulsions

The Crosslinked Aminosilicone Polymer described above may be in an emulsion. Alternatively, the Crosslinked Aminosilicone Polymer described above may be prepared by emulsion polymerization and thereafter isolated. The isolated Crosslinked Aminosilicone Polymer may be an ingredient in an emulsion composition. The emulsion composition generally comprises (A) the Crosslinked Aminosilicone Polymer described above, (B) a surfactant, and (C) water. As used herein, "emulsion" is meant to encompass water continuous emulsions, for example an oil in water type emulsion, or a silicone in water emulsion (s/w), oil or silicone continuous emulsions, for example water in oil emulsions or water in silicone emulsions (w/s), or multiple phase emulsions (water/oil/water, oil/water/oil types, water/silicone/water, or silicone/water/silicone). The Crosslinked Aminosilicone Polymer may be added to any type of emulsion by common mixing techniques. The addition the Crosslinked Aminosilicone Polymer may occur either during the preparation of the emulsion, or subsequently post added to a pre-formed emulsion. Alternatively, the Crosslinked Aminosilicone Polymer may be formed in situ via emulsion polymerization. There are no special requirements or conditions needed to effect the mixing of the Crosslinked Aminosilicone Polymer and the emulsion. Mixing techniques can be simple stirring, homogenizing, sonolating, and other mixing techniques known in the art to effect the formation of emulsions. The mixing can be conducted in a batch, semi-continuous, or continuous process.

The amount of Crosslinked Aminosilicone Polymer added to the emulsion can vary and is not limited, however the amounts typically may range from a Crosslinked Aminosilicone Polymer/emulsion weight ratio of 0.1/99 to 99/0.1, alternatively 1/99 to 99/1. Generally, the silicone emulsions contain a Crosslinked Aminosilicone Polymer concentration of 10% to 70% based on the weight of the emulsion, alternatively 20% to 60%. While emulsions containing less than 10% Crosslinked Aminosilicone Polymer content can be made, such emulsions may have little or no economic value. The surfactant is generally present at 0.05% to 30% based on the weight of the emulsion, alternatively 0.1% to 20%. Water (and additional ingredients, if present) may constitute the balance of the emulsion to 100%.

Anionic Surfactant

Alternatively, the emulsion containing the Crosslinked Aminosilicone Polymer may contain anionic surfactants, cationic surfactants, amphoteric surfactants, and nonionic surfactants. The anionic surfactants include (i) sulfonic acids and their salt derivatives, including alkyl, aralkyl, alkyl naphthalene, alkyl diphenyl ether sulfonic acids, and their salts, having at least 6 carbon atoms in the alkyl substituent, such as dodecyl benzene sulfonic acid, and its sodium salt or its amine salt; (ii) alkyl sulfates having at least 6 carbon atoms in the alkyl substituent, such as sodium lauryl sulfate; (iii) the sulfate esters of polyoxyethylene monoalkyl ethers; (iv) long chain carboxylic acid surfactants and their salts, such as lauric acid, steric acid, oleic acid, and their alkali metal and amine salts. Some other examples of anionic surfactants are alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates; ether sulfates having alkyl groups of eight or more carbon atoms such as sodium lauryl ether sulfate; and alkylaryl sulfonates having one or more alkyl groups of eight or more carbon atoms such as neutral salts of hexadecylbenzene sulfonic acid and $C_{20}$ alkylbenzene sulfonic acid.

Commercial anionic surfactants which can be used include the sodium salt of dodecyl benzene sulfonic acid sold under the trademark SIPONATE® DS-10 by Alcolac Inc., Baltimore, Md.; sodium n-hexadecyl diphenyloxide disulfonate sold under the trademark DOWFAX® 8390 by The Dow Chemical Company, Midland, Mich.; the sodium salt of a secondary alkane sulfonate sold under the trademark HOSTAPUR® SAS 60 by Clariant Corporation, Charlotte, N.C.; N-acyl taurates such as sodium N-lauroyl methyl taurate sold under the trademark NIKKOL LMT® by Nikko Chemicals Company, Ltd., Tokyo, Japan; and linear alkyl benzene sulfonic acids sold under the trademark BIOSOFT® S-100 by the Stepan Company, Northfield, Ill. Compositions of the latter type such as dodecyl benzene sulfonic acid, although a catalyst as noted above, can also function as the anionic surfactant when neutralized. Other suitable surfactants include sodium alkyl sulfonate such as HOSTAPUR® SAS-30. In one embodiment, the emulsifier is triethanolamine dodecyl benzene sulfonate, such as BIOSOFT® N 300.

Cationic Surfactant

Cationic surfactants useful herein include compounds containing quaternary ammonium hydrophilic moieties in the molecule which are positively charged, such as quaternary ammonium salts represented by $R^8R^9R^{10}R^{11}N^+X^-$ where $R^8$ to $R^{11}$ are alkyl groups containing 1-30 carbon atoms, or alkyl groups derived from tallow, coconut oil, or soy; and X is a halogen, e.g., chlorine or bromine. Alternatively, the quaternary ammonium compounds may be alkyl trimethylammonium and dialkyldimethylammonium halides, or acetates, or hydroxides, having at least 8 carbon atoms in each alkyl substituent. Dialkyl dimethyl ammonium salts can be used and are represented by $R^{12}R^{13}N^+(CH_3)_2X^-$ where $R^{12}$ and $R^{13}$ are alkyl groups containing 12-30 carbon atoms or alkyl groups derived from tallow, coconut oil, or soy; and X is halogen. Monoalkyl trimethyl ammonium salts can be used and are represented by $R^{14}N^+(CH_3)_3X^-$ where $R^{14}$ is an alkyl group containing 12-30 carbon atoms or an alkyl group derived from tallow, coconut oil, or soy; and X is halogen, acetate, or hydroxide.

Representative quaternary ammonium halide salts are dodecyltrimethyl ammonium chloride/lauryltrimethyl ammonium chloride (LTAC), cetyltrimethyl ammonium chloride (CTAC), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, and didocosyldimethyl ammonium chloride. These quaternary ammonium salts are commercially available under trademarks such as ADOGEN®, ARQUAD®, TOMAH®, and VARIQUAT®.

Other suitable cationic surfactants which can be used include (i) fatty acid amines and amides and their salts and derivatives, such as aliphatic fatty amines and their derivatives. Such cationic surfactants that are commercially available include compositions sold under the names Arquad T27 W, Arquad 16-29, by Akzo Nobel Chemicals Inc., Chicago, Ill.; and Ammonyx Cetac-30 by the Stepan Company, Northfield, Ill.

Amphoteric Surfactant

Suitable amphoteric surfactants include; betaines such as cocamidopropylbetaine, sultaines such as cocamidopropylhydroxysultaine, lecithin and hydrogenated lecithin, In one embodiment, the emulsifier is a combination of an anionic and nonionic surfactant. In a further embodiment, the anionic surfactant in the combination is an alkyl sulfonate or a dodecyl benzene sulfonate. In a further embodiment, the nonionic emulsifier is an alkyl-oxo alcohol polyglycol ether or an alkyl polyethylene glycol ether.

Non-Ionic Surfactant

Some suitable nonionic surfactants which can be used include polyoxyethylene alkyl ethers, polyoxyethylene alkyl phenyl ethers, alkylglucosides, polyoxyethylene fatty acid esters, sorbitan fatty acid esters, and polyoxyethylene sorbitan fatty acid esters. Nonionic surfactants which are commercially available include compositions such as (i) 2,6,8-trimethyl-4-nonyl polyoxyethylene ether sold under the names Tergitol TMN-6 and Tergitol TMN-10; (ii) the C11-15 secondary alkyl polyoxyethylene ethers sold under the names Tergitol 15-S-7, Tergitol 15-S-9, Tergitol 15-S-15, Tergitol 15-S-30, and Tergitol 15-S-40, by the Dow Chemical Company, Midland, Mich.; octylphenyl polyoxyethylene (40) ether sold under the name Triton X405 by the Dow Chemical Company, Midland, Mich.; (iii) nonylphenyl polyoxyethylene (10) ether sold under the name Makon 10 by the Stepan Company, Northfield, Ill.; (iv) ethoxylated alcohols sold under the name Trycol 5953 by Henkel Corp./Emery Group, Cincinnati, Ohio; (v) ethoxylated alcohols sold under the name Brij L23 and Brij L4 by Croda Inc. Edison, N.J., (vi) alkyl-oxo alcohol polyglycol ethers such as ®GENAPOL UD 050, and Genapol UD110, (vii) alkyl polyethylene glycol ether based on C10-Guerbet alcohol and ethylene oxide such as LUTENSOL® XP 79.

Suitable nonionic surfactants also include poly(oxyethylene)-poly(oxypropylene)-poly(oxyethylene) tri-block copolymers. Poly(oxyethylene)-poly(oxypropylene)-poly(oxyethylene) tri-block copolymers are also commonly known as Poloxamers. They are nonionic triblock copolymers composed of a central hydrophobic chain of polyoxypropylene (poly(propylene oxide)) flanked by two hydrophilic chains of polyoxyethylene (poly(ethylene oxide)). Poly(oxyethylene)-poly(oxypropylene)-poly(oxyethylene) tri-block copolymers are commercially available from BASF (Florham Park, N.J.) and are sold under the tradename PLURONIC®, such as Pluronic L61, L62, L64, L81, P84.

Other suitable nonionic surfactants include polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants. Commercially available nonionic surfactants which can be used include compositions such as 2,6,8-trimethyl-4-nonyloxy polyethylene oxyethanols (6EO) and (10EO) sold under the trademarks TERGITOL® TMN-6 and TERGITOL® TMN-10; alkyleneoxy polyethylene oxyethanol ($C_{11-15}$ secondary alcohol ethoxylates 7EO, 9EO, and 15EO) sold under the trademarks TERGITOL®15-S-7, TERGITOL®15-S-9, TERGITOL®15-S-15; other $C_{11-15}$ secondary alcohol ethoxylates sold under the trademarks TERGITOL®15-S-12, 15-S-20, 15-S-30, 15-S-40; and octylphenoxy polyethoxy ethanol (40EO) sold under the trademark TRITON® X-405. All of these surfactants are sold by Union Carbide Corporation, Danbury, Conn.

Other useful commercial nonionic surfactants are nonylphenoxy polyethoxy ethanol (10EO) sold under the trademark MAKON® 10 by Stepan Company, Northfield, Ill.; polyoxyethylene 23 lauryl ether (Laureth-23) sold commercially under the trademark BRIJ® 35L by ICI Surfactants, Wilmington, Del.; and RENEX® 30, a polyoxyethylene ether alcohol sold by ICI Surfactants, Wilmington, Del.

The nonionic surfactant may also be a silicone polyether (SPE). The silicone polyether as an emulsifier may have a rake type structure wherein the polyoxyethylene or polyoxyethylene-polyoxypropylene copolymeric units are grafted onto the siloxane backbone, or the SPE can have an ABA block copolymeric structure wherein A represents the polyether portion and B the siloxane portion of an ABA structure. Suitable silicone polyethers include Dow Corning® 5329 from Dow Corning Corporation of Midland, Mich. USA. Alternatively, the nonionic surfactant may be selected from polyoxyalkylene-substituted silicones, silicone alkanolamides, silicone esters and silicone glycosides. Such silicone-based surfactants may be used to form such emulsions and are known in the art, and have been described, for example, in U.S. Pat. No. 4,122,029 to Gee et al., U.S. Pat. No. 5,387,417 to Rentsch, and U.S. Pat. No. 5,811,487 to Schulz et al.

Other suitable nonionic surfactants include SYNPERONIC 13/6 and 13/12.

Water in Oil Emulsion

In one embodiment, the emulsion is a water-in-silicone emulsion and contains a water-in-silicone surfactant. In this embodiment, the water-in-silicone surfactant may be nonionic and may be selected from polyoxyalkylene-substituted silicones, silicone alkanolamides, silicone esters and silicone glycosides, as described above.

Oil-in-Water Emulsion

Alternatively, when the emulsion is an oil-in-water emulsion, it may include nonionic surfactants known in the art to prepare o/w emulsions. Suitable nonionic surfactants for this embodiment are exemplified by the polyoxyethylene alkyl ethers, polyoxyethylene alkylphenol ethers, polyoxyethylene lauryl ethers, polyoxyethylene sorbitan monooleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants, as described above.

Additional Ingredients for Emulsions

One or more additional ingredients (D) may be added to the emulsions described above. Such additional ingredients may be selected from (i) a protective colloid, (ii) a preservative (e.g., biocide), (iii) a rust inhibitor, (iv) freeze inhibitor (e.g., propylene glycol), (v) a pH adjusting agent, and combinations of two or more of (i), (ii), (iii), (iv), and (v).

Protective colloids, i.e., colloidal stabilizers, may be used, if desired, to enhance stability or to provide a specific rheological characteristic to the emulsion. As used herein, the terms "protective colloid" and/or "colloidal stabilizer" mean a nonionic molecule that is an effective agent for protecting charged colloidal particles in an aqueous media against flocculation. These compositions typically have a weight average molecular weight ranging from 1,000-300,000 and are typically more hydrophilic than the composition of the first emulsion polymer, as measured by weight-averaged solubility parameters. Colloidal stabilizers which can be used include hydroxyethyl cellulose having a weight average molecular weight between 50,000-150,000; N-vinyl pyrrolidone; polyvinyl alcohol having a weight average molecular weight between 10,000-200,000; partially acetylated polyvinyl alcohol; carboxymethyl cellulose; gums such as gum arabic; starches; proteins; and mixtures thereof. Preferred colloidal stabilizers are hydroxyethyl cellulose and polyvinyl alcohol.

Since emulsions are susceptible to microbiological contamination a preservative can be added. Representative preservatives, which can be used include phenoxyethanol and ethylhexylglycerin; formaldehyde; 1,3-dimethylol-5,5-dimethyl hydantoin, e.g., DMDM Hydantoin; 5-bromo-5-nitro-1,3-dioxane; methyl or propyl paraben; sorbic acid; imidazolidinyl urea; and KATHON® CG (5-chloro-2-methyl-4-isothiazolin-3-one); caprylyl glycol; phenoxyethanol; benzyl alcohol; and/or benzoic acid.

Suitable freeze inhibitors are known in the art and are commercially available. The freeze inhibitor can be a glycol, such as propylene glycol.

Suitable pH adjusters can be any acid or base that does not react with starting material (ii). Suitable acids include acetic acid, maleic acid, or lactic acid. Suitable bases include a tertiary amine, e.g., triethanolamine. Acids and bases suitable as pH adjusters are known in the art and are commercially available.

Method for Treating Fibers

This invention further relates to a treatment method comprising applying to a substrate (e.g., a textile or other fiber) the Crosslinked Aminosilicone Polymer or emulsion thereof, either of which are also referred herein as the Treatment Composition. The amount applied is a "hand improving" effective amount of the Treatment Composition and is applied to the fiber and/or textile and/or other substrate by any convenient method. The term "Hand" as used herein means the softness and smoothness of the substrate, e.g., fabric. For example, the Treatment Composition can be applied by padding, dipping, spraying or exhausting. When the Treatment Composition comprises more than one solution, dispersion, or emulsion; the solutions, dispersions, and emulsions can be applied simultaneously or sequentially to the substrates, e.g., textiles. After the Treatment Composition is applied to the substrate, e.g., fiber and/or fabric, it can be dried under ambient conditions or by heating.

The Treatment Composition can be applied to the substrate, e.g., fiber and/or textile during making the fibers or textiles, or later such as during laundering textiles. After application, carriers (if any) can be removed from the Treatment Composition for example by drying the composition at ambient or elevated temperature. The amount of Treatment Composition applied to the substrate, e.g., fibers and textiles is typically sufficient to provide 0.1 to 15 weight percent of the composition on the substrate, based on the dry weight of the substrate, alternatively in an amount of 0.2 to 5 weight percent based on the dry weight of the substrate.

Fibers and textiles that can be treated with the Treatment Composition include natural fibers such as cotton, silk, linen, and wool; regenerated fibers such as rayon and acetate; synthetic fibers such as polyesters, polyamides, polyacrylonitriles, polyethylenes, and polypropylenes; combinations, and blends thereof. The form of the fibers can include threads, filaments, tows, yarns, woven fabrics, knitted materials, non-woven materials, paper, and carpet. Without wishing to be bound by theory, it is thought that textiles treated with the Crosslinked Aminosilicone Polymer have a feel or hand comparable to conventional hydrophobic silicone, but do not significantly impact negatively on the hydrophilicity of the textile.

The Treatment Composition may be added to a fiber or textile treatment composition such as a fabric softener or a laundry detergent. The Crosslinked Aminosilicone Polymer described herein is useful in a fabric softener composition comprising:
(A) the Crosslinked Aminosilicone Polymer described above or the emulsion thereof described above,
(B) water,
(C) a fragrance,
(D) a cationic surfactant (e.g., an ester quat), and
optionally (E) a thickener.

Personal Care Products

The Treatment Composition may alternatively be formulated into personal care products. Generally, such products can generally be prepared at room temperature if no solid materials at room temperature are presents in the compositions, using simple propeller mixers, Brookfield counter-rotating mixers, or homogenizing mixers. No special equipment or processing conditions are typically required. Depending on the type of form made, the method of preparation will be different, but such methods are known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners (either leave in or rinse off), hair colorants, hair relaxants, hair styling aids such as sprays, fixatives, mousses, and/or gels; permanents, depilatories, and cuticle coats, make-ups, color cosmetics, foundations, concealers, blushes, lipsticks, eyeliners, mascara, oil removers, color cosmetic removers, powders, medicament creams, pastes or sprays including dental hygienic, antibiotic, healing promotive, and/or nutritive, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier would be apparent to one of ordinary skill in the art.

The Treatment Composition can be used in a variety of personal, household, and healthcare applications. In particular, the Treatment Composition may be used in the personal care products disclosed in U.S. Pat. No. 6,051,216 to Barr et al.; U.S. Pat. No. 5,919,441 to Mendolia et al.; U.S. Pat. No. 5,981,680 to Petroff et al.; as disclosed in U.S. Patent Application 2010/0098648 to Yu. and WO 2004/060101 to Yu; in sunscreen compositions as disclosed in U.S. Pat. No. 6,916,464 to Hansenne et al.; in cosmetic compositions also containing film-forming resins, as disclosed in WO2003/105801 to Yu; in the cosmetic compositions as disclosed in U.S. Patent Application 2003/0235553 to Lu, U.S. Patent Application 2003/0072730 to Tornilhac, U.S. Patent Application 2003/0170188 to Ferrari et al., EP 1,266,647 to Tornilhac, EP 1,266,648 to Ferrari, et al., EP1,266,653 to Ferrari et al., WO2003/105789 to Lu, WO2004/000247 to Lu and WO2003/106614 to Lu; as additional agents to those disclosed in WO2004/054523 to Tournilhac; in long wearing cosmetic compositions as disclosed in US Patent Application Publication 2004/0180032; in transparent or translucent care and/or make up compositions as discussed in WO 2004/054524; all of which are incorporated herein by reference.

The personal care products according to this invention can be used by standard methods, such as applying them to the human body, e.g., skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care products according to the present invention may be used in a conventional manner for example for conditioning the skin. An effective amount of the composition for the purpose is applied to the skin. Such effective amounts generally range from 1 mg/cm$^2$ to 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the personal care products according to the invention on hair may use a conventional manner for conditioning hair. An effective amount of the composition for conditioning hair is applied to the hair. Such effective amounts generally range from 0.5 g to 50 g, alternatively from 1 g to 20 g. Application to the hair typically includes working the composition through the hair such that most or all of the hair is contacted with the product. This method for conditioning the hair comprises the steps of applying an effective amount of the hair care product to the hair, and then working the composition through the hair. These steps can be repeated as many times as desired to achieve the desired conditioning benefit.

Non-limiting examples of additives which may be formulated into the personal care products in addition to the Treatment Composition include: (i) additional silicones, (ii) anti-oxidants, (iii) cleansing agents, (iv) colorants, (v) additional conditioning agents, (vi) deposition agents, (vii) electrolytes, (viii) emollients, (ix) additional oils, (x) exfoliating agents, (xi) foam boosters, (xii) fragrances, (xiii) humectants, (xiv) occlusive agents, (xv) pediculicides, (xvi) pH control agents, (xvii) pigments, (xviii) preservatives (in addition to or instead of the preservative described above, when the Treatment Composition is an emulsion containing a preservative), (xix) biocides, other solvents, (xx) stabilizers, (xxi) sun-screening agents, (xxii) suspending agents, (xxiii) tanning agents, (xxiv) other surfactants (e.g., in addition to or instead of the surfactant present when the Treatment Composition is an emulsion), (xxv) thickeners, (xxvi) vitamins, (xxvii) botanicals, (xxviii) waxes, (xxix) rheology-modifying agents, (xxx) anti-dandruff, (xxxi) antiacne, (xxxii) anti-carie, and (xxxiii) wound healing-promotion agents, and any two or more of (i) to (xxxiii).

The personal care product, such as a shampoo or cleanser may contain at least one anionic detersive surfactant. This can be any of the well-known anionic detersive surfactants typically used in shampoo formulations. These anionic detersive surfactants function as cleansing agents and foaming agents in the shampoo compositions of this invention. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Alternatively, the detersive surfactant is selected from the group consisting of sodium lauryl sulfate, ammonium lauryl sulfate, triethanolamine lauryl sulfate, sodium lauryl ether sulfate, and ammonium lauryl ether sulfate. The anionic detersive surfactant is present in the shampoo compositions of this invention in an amount from 5% to 50% and alternatively 5% to 25% based on the total weight of the personal care product.

The personal care product may contain at least one cationic deposition aid, alternatively a cationic deposition polymer. The cationic deposition aid may be present in amounts ranging from 0.001% to 5%, alternatively 0.01% to 1%, and alternatively 0.02% to 0.5% based on total weight of all ingredients in the personal care product. The cationic deposition polymer may be a homopolymer or be formed from two or more types of monomers. The molecular weight of the cationic deposition polymer may be at least 10,000, alternatively may range from 5,000 to 10,000,000, alternatively, and alternatively 100,000 to 2,000,000. The cationic deposition polymers will have cationic nitrogen containing groups such as quaternary ammonium or protonated amino groups, or a mixture thereof. The cationic charge density may be at least 0.1 meq/g, alternatively above 0.8 or higher. The cationic charge density should not exceed 4 meq/g, it is alternatively less than 3; and alternatively less than 2 meq/g. The charge density can be measured using the Kjeldahl method and should be within the above limits at the desired pH of use, which may range from 3 to 9; alternatively 4 to 8. The cationic nitrogen-containing group will generally be present as a substituent on a fraction of the total monomer units of the cationic deposition polymer. Thus when the cationic deposition polymer is not a homopolymer it can contain spacer noncationic monomer units. Such polymers are described in the CTFA Cosmetic Ingredient Directory, 3rd edition. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers may have alkyl groups of 1 to 7 carbon atoms, alternatively alkyl groups of 1 to 3 carbon atoms. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, alternatively tertiary may be used. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers may be lower alkyls such as the alkyl groups of 1 to 4 carbon atoms, alternatively alkyl groups of 1 to 2 carbon atoms. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide. The cationic deposition aids can comprise mixtures of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256 to Nowak Jr., et al.; and cationic polyacrylamides as described in U.S. Pat. No. 5,543,074 to Hague et al. Other cationic deposition aids that can be used include polysaccharide polymers, such as cationic cellulose derivatives and cationic starch derivatives. Cationic polysaccharide polymer materials suitable for use in compositions of the invention include those of the formula: $-O(R^{15}-N+R^{16}R^{17}R^{18}X-)$ wherein: A is an anhydroglucose residual group, such as starch or cellulose anhydroglucose residual, $R^{15}$ is an alkylene oxyalkylene, polyoxyalkylene, or hydroxyalkylene group, or combination thereof, $R^{16}$, $R^{17}$ and $R^{18}$ independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in $R^{16}$, $R^{17}$ and $R^{18}$) may 20 or less, and X is an anionic counterion, as previously described. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418 to Birkofer, incorporated by reference herein), and copolymers of etherified cellulose and starch (e.g., as described in U.S. Pat. No. 3,958,581 to Abegg et al., incorporated by reference herein).

The personal care product may contain a foam boosting agent. A foam booster is an agent which increases the amount of foam available from a system at a constant molar concentration of surfactant, in contrast to a foam stabilizer which delays the collapse of a foam. Foam building is provided by adding to the aqueous media an effective amount of a foam boosting agent. The foam boosting agent may be selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Alternatively, a foam booster may be selected from the group consisting of lauric acid diethanolamide, N-lauryl dimethylamine oxide, coconut acid diethanolamide, myristic acid diethanolamide, and oleic acid diethanolamide. The foam boosting agent may be present in the shampoo compositions of this invention in an amount of 1% to 15%, alternatively 2% to 10% based on the total weight of the shampoo composition. The shampoo composition may further comprise a polyalkylene glycol to improve lather performance. Concentration of the polyalkylene glycol in the shampoo composition may range from 0.01% to 5%, alternatively from 0.05% to 3%, and alternatively 0.1% to 2%, by weight of the composition. The optional polyalkylene glycols are characterized by the general formula: $H(OCH_2CHR^{19})_t$—OH where $R^{19}$ is selected from the group consisting of H, methyl, and mixtures thereof. When $R^{19}$ is H, these materials are polymers of ethylene oxide, which are also known as polyethylene oxides, polyoxyethylenes, and polyethylene glycols. When $R^{19}$ is methyl, these materials are polymers of propylene oxide, which are also known as polypropylene oxides, polyoxypropylenes, and polypropylene glycols. When $R^{19}$ is methyl, it is also understood that various positional isomers of the resulting polymers can exist. In the above structure, subscript t has an average value of 1,500 to 25,000, alternatively 2,500 to 20,000, and alternatively 3,500 to 15,000. Polyethylene glycol polymers useful herein are PEG-2M wherein $R^{19}$ equals H and subscript t has an average value of 2,000 (PEG-2M is also known as Polyox WSR9 N-10, which is available from Union Carbide and as PEG-2,000); PEG-5M wherein $R^{19}$ equals H and t has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein $R^{19}$ equals H and t has an average value of 7,000 (PEG-7M is also known as Polyox WSRO N-750 available from Union Carbide); PEG-9M where $R^{19}$ equals H and t has an average value of 9,000 (PEG 9-M is also known as Polyox WSRS N-3333 available from Union Carbide); and PEG14 M wherein $R^{19}$ equals H and t has an average value of 14,000 (PEG-14M is also known as Polyox WSRO N-3000 available from Union Carbide). Other useful polymers include the polypropylene glycols and mixed polyethylene/polypropylene glycols.

The personal care product may contain a suspending agent at concentrations effective for suspending the Cross-linked Aminosilicone Polymer, and/or other water-insoluble ingredient, in dispersed form in the shampoo compositions. Such concentrations range from 0.1% to 10%, alternatively from 0.3% to 5.0%, by weight of the shampoo compositions. Suspending agents include crystalline suspending agents which can be categorized as acyl derivatives, long chain amine oxides, and mixtures thereof, concentrations of which range from 0.1% to 5.0%, alternatively from 0.5% to 3.0%, by weight of the shampoo compositions. These suspending agents are described in U.S. Pat. No. 4,741,855 to Grote et al., which description is incorporated herein by reference. These suspending agents include ethylene glycol esters of fatty acids alternatively having from 16 to 22 carbon atoms. Alternatively, the suspending agents are the ethylene glycol stearates, both mono and distearate, but particularly the distearate containing less than 7% of the mono stearate. Other suitable suspending agents include alkanol amides of fatty acids, having from 16 to 22 carbon atoms, alternatively 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the materials listed above may be used as suspending agents. For example, it is contemplated that suspending agents with long chain hydrocarbyls having 8 to 22 carbon atom chains may be used. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g., stearyl dimethyl amine oxide. Other suitable suspending agents include xanthan gum at concentrations ranging from 0.3% to 3%, alternatively 0.4% to 1.2%, by weight of the shampoo compositions. The use of xanthan gum as a suspending agent in silicone containing shampoo compositions is described, for example, in U.S. Pat. No. 4,788,006 to Bolich et al., which description is incorporated herein by reference. Combinations of long chain acyl derivatives and xanthan gum may also be used as a suspending agent in the shampoo compositions. Such combinations are described in U.S. Pat. No. 4,704,272 to Oh et al., which description is incorporated herein by reference. Other suitable suspending agents include carboxyvinyl polymers. Among these polymers are the copolymers of acrylic acid crosslinked with polyallylsucrose as described in U.S. Pat. No. 2,798,053 to Brown, which description is incorporated herein by reference. Examples of these polymers include Carbopol 934, 940, 941, and 956, available from B. F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, viscosity modifiers, and gelling agents.

The personal care composition may contain one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care product may contain various additional oils (i.e., in addition to the Crosslinked Aminosilicone Polymer). The term "oil" as used herein refers to any material which is substantially insoluble in water. When the Treatment Composition is to be used in a cosmetic or other personal care product, the product ingredients must also be cosmetically acceptable or otherwise meet the conditions of the end use product. Suitable oils include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelargonate; and triesters, such as glyceryl trioctanoate and silicones especially cyclomethicone and dimethicone and mixtures thereof. The Treatment Composition, may also contain oils, alternatively a mixture of low viscosity and high viscosity oils. Suitable low viscosity oils have a viscosity of 5 to 100 mPa·s at 25° C., and may be esters having the structure $R^{20}CO-OR^{21}$ wherein $R^{20}CO$ represents the carboxylic acid radical and wherein $OR^{21}$ is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., alternatively a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. The suggested ratio of low viscosity to high viscosity oils in the oil phase is 1:15 to 15:1, alternatively 1:10 to 10:1 respectively. Alternatively, the personal care product may comprise 1% to 20% of a mixture of low viscosity and high viscosity surface oils.

Among the additional oils, mineral oils, such as liquid paraffin or liquid petroleum, of animal oils, such as perhydrosqualene or arara oil, or alternatively vegetable oils, such as sweet almond, calophyllum, palm, castor, avocado, jojaba, olive or cereal germ oil may be added to a personal care product containing the Treatment Composition. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care product may contain various waxes. The waxes generally have a melting point range of 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. Animal waxes, such as beeswax; vegetable waxes, such as carnauba, candelilla, ouricury or japan wax or cork fibre or sugarcane waxes; mineral waxes, for example paraffin or lignite wax or microcrystalline waxes; synthetic waxes, including polyethylene waxes, and waxes obtained by the Fischer-Tropsch synthesis are also suitable. Silicone waxes (in addition to the other ingredients of the personal care composition) may be used, such as waxes of polymethylsiloxane alkyls, alkoxys and/or esters.

A thickening agent may be added to provide a convenient viscosity. For example, viscosities of 500 mm$^2$/s to 25,000 mm$^2$/s at 25° C. or alternatively 3,000 to 7,000 mm$^2$/s are usually suitable. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methylhydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or mixtures of 2 or more of these. Alternatively the thickening agent is selected from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, is used in shampoos in an amount sufficient to provide a viscosity in the shampoo of 500 $mm^2$/s to 25,000 $mm^2$/s. Alternatively the thickening agent may be present in an amount from 0.05% to 10% and alternatively 0.05% to 5% based on the total weight of the shampoo composition.

Stabilizing agents can be used in the water phase of the personal care product containing the Treatment Composition. Suitable water phase stabilizing agents can include alone or in combination one or more electrolytes, polyols, alcohols such as ethyl alcohol, and hydrocolloids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it may amount to 0.1% to 5% and alternatively 0.5% to 3% of the total composition. The hydrocolloids include gums, such as Xanthan gum or Veegum and thickening agents, such as carboxymethyl cellulose. Polyols, such as glycerine, glycols, and sorbitols can also be used. Alternative polyols are propylene glycol, sorbitol and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xanthan gum.

The personal care product can also be under the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions other than the Treatment Composition described above, may also be included in the personal care products. For example, such silicones include; silicone fluids, gums, resins, elastomers; silicone surfactants and emulsifiers such as silicone polyethers, organofunctional silicones such as aminofunctional silicones and alkylmethylsiloxanes.

Alkylmethylsiloxanes may be included in the present compositions. These siloxane polymers may have the formula $Me_3SiO[Me_2SiO]_w[MeR^{22}SiO]_zSiMe_3$, in which $R^{22}$ is a hydrocarbon group containing 6-30 carbon atoms, Me represents methyl, subscript w≥0, subscript z>0, and the DP, i.e., the sum of w and z is 3 to 50. Both the volatile and liquid species of alkymethysiloxanes can be used in the composition.

Silicone gums may be included in the present compositions. Polydiorganosiloxane gums are known in the art and are available commercially. They consist of generally insoluble polydiorganosiloxanes having a viscosity in excess of 1,000,000 $mm^2$/s at 25° C., alternatively greater than 5,000,000 $mm^2$/s at 25° C. These silicone gums may be sold as compositions already dispersed in a suitable solvent to facilitate their handling. Ultra-high viscosity silicones can also be included as optional ingredients. These ultra-high viscosity silicones typically have a kinematic viscosity greater than 5 million $mm^2$/s at 25° C., to 20 million $mm^2$/s at 25° C. Compositions of this type in the form of suspensions may be used, and are described for example in U.S. Pat. No. 6,013,682 to Dalle, et al.

Silicone resins may be included in the present personal care products. These resins are generally highly crosslinked polymeric siloxanes. Crosslinking is obtained by incorporating trifunctional and/or tetrafunctional silanes with the monofunctional silane and/or difunctional silane monomers used during manufacture. The degree of crosslinking required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of crosslinking to dry down to a rigid or a hard film can be considered to be suitable for use as the silicone resin. Commercially available silicone resins suitable for applications herein are generally supplied in an unhardened form in low viscosity volatile or nonvolatile silicone fluids. The silicone resins should be incorporated into compositions of the invention in their non-hardened forms rather than as hardened resinous structures.

Silicone carbinol fluids may be included in the present compositions. These materials are described in U.S. Patent Application 2004/0223936 to Fecht, et al. and can be commonly described as substituted hydrocarbyl functional siloxane fluids or resins.

When selecting ingredients for the Treatment Composition and/or the personal care product described above, there may be overlap between types of ingredients because certain ingredients described herein may have more than one function. For example, hydroxyethylcellulose may be useful as a colloidal stabilizer and a thickening agent. When adding additional ingredients to the Treatment Composition and/or the personal care product, the additional ingredients are distinct from one another.

Exemplary hair care products that can be made with the Crosslinked Aminosilicone Polymer described above include a shampoo comprising:
(1) the Crosslinked Aminosilicone Polymer described above, or the emulsion of the Crosslinked Aminosilicone Polymer described above,
(2) water, and
(3) an anionic surfactant and/or an amphoteric surfactant (e.g., sodium laureth sulfate),
optionally (4) a preservative, and
optionally (5) a cationic deposition polymer, and
optionally (6) a thickener (e.g., carbomer).

Alternatively, the hair care product may be a hair conditioner comprising:
(A) the Crosslinked Aminosilicone Polymer described above, or the emulsion of the Crosslinked Aminosilicone Polymer described above,
(B) water,
optionally (C) a thickener (e.g., Hydroxyethyl-cellulose),
(D) a fatty alcohol (e.g., Cetearyl Alcohol),
optionally (E) other emulsifiers (e.g., PEG-100 Stearate & Glyceryl Stearate),
optionally (F) a preservative, and
optionally (G) a cationic surfactant.

Alternatively, the emulsion described above may be used as a leave in hair treatment or styling composition.

Alternatively, the hair care composition may be an anhydrous leave in hair treatment composition comprising:
(A) the Crosslinked Aminosilicone Polymer described above, and
(B) an organic or silicone carrier.

Alternatively, the hair care composition may be a styling aid, such as a styling mousse, comprising:
(A) the Crosslinked Aminosilicone Polymer or an emulsion thereof, as described above, and
(B) water,
optionally (C) a thickener,
optionally (D) an additional emulsifier,
optionally (E) a cationic polymer,
optionally (F) an organic styling polymer, and
optionally (G) a preservative.

EXAMPLES

These examples are intended to illustrate the invention to one of ordinary skill in the art and should not be interpreted as limiting the scope of the invention set forth in the claims. Reference examples should not be deemed as prior art unless so indicated. All measurements and experiments were conducted at 23° C., unless indicated otherwise.

The following surfactants were used in the examples herein. Genapol UD 050 was a commercially available nonionic surfactant with an HLB value of 11.4. Genapol UD 110 was a commercially available nonionic surfactant with an HLB value of 14.4. Brij L4 was a commercially available nonionic surfactant with an HLB value of 9.7. Brij L23 was a commercially available nonionic surfactant with an HLB value of 16.9. Tergitol 15S5 was a commercially available nonionic surfactant with an HLB value of 10.5. Tergitol 15S15 was a commercially available nonionic surfactant with an HLB value of 15.4. Lutensol XP 50 was a commercially available nonionic surfactant with an HLB value of 10. Lutensol XP 140 was a commercially available nonionic surfactant with an HLB value of 16.

Example 1: Crosslinked Aminosiloxane—Emulsion A

Into a 1 L flask was weighed 300 g of a trimethyl-siloxy terminated pendant Amino Siloxane Polymer having 6.9 mole of NH per 100 DP and having average unit formula: $(Me_3SiO_{1/2})_2(Me_2SiO_{2/2})_{392}(MeR4SiO_{2/2})_9$, where each Me represents a methyl group and R4 is an aminofunctional group of formula:

where D12 is a iso-butyl group and D13 is an ethylene group; followed by 40 g of Genapol UD 050 and 90 g of Genapol UD 110. The flask was equipped with a Teflon stir paddle, a condenser, and a temperature probe. The mixture was heated to 70° C. with mixing at 200 rpm. 145 g of water and 2 g of acetic acid were added and kept heating to 70° C. Thereafter, 6 g of glycidol was added and mixed at 400 rpm for 2 hrs. Then 4.6 g of epoxytrimethoxysilane was added and kept at 70° C. for ½ hr with mixing at 400 rpm. The balance of water was added to give a total of 1000 g of emulsion. The resulting emulsion was an aqueous emulsion of amino polymer siloxane having 30% active (i.e., 30% Crosslinked Aminosilicone Polymer). Particle size of emulsion was at 20-50 nanometer at median diameter measured in volume mode. The emulsion was dried at room temperature, resulting in a dry film, Rheological profile of dried film was measured on Rheometer.

Example 2: Crosslinked Aminosiloxane—Emulsion B

Into a 1 L flask was weighed 300 g of pendant Amino Siloxane Polymer (6.9 mole of NH per 100 DP) followed by 40 g of Genapol UD 050 and 90 g of Genapol UD 110. The flask was equipped with a Teflon stir paddle, a condenser, and a temperature probe. The mixture was heated to 70° C. with mixing at 200 rpm. 145 g of water and 2 g of acetic acid were added and kept heating to 70° C. 6 g of glycidol was added and mixed at 400 rpm for 2 hrs. Then 6.9 g of epoxytrimethoxysilane was added and kept at 70° C. for ½ hr with mixing at 400 rpm. The balance of water was added to give a total of 1000 g of emulsion. The resulting emulsion was an aqueous emulsion of amino polymer siloxane having 30% active. Particle size of emulsion was at 20-50 nanometer at median diameter measured in volume mode. The emulsion was dried at room temperature, resulting in a dry film, Rheological profile of dried film was measured on Rheometer.

Comparative Example 1

Into a 100 Max cup was weighed 20 g of Dimethyl, Methyl Aminoethylaminoisobutyl siloxane, methoxy & hydroxy terminated with an amine number of 0.13 and a viscosity of 4255 centiPoise (manufactured by Dow) followed by 0.19 g of N-morpholinomethyl-triethoxysilane, 6.5 g of isotridecyl pentaethoxylate, commercially available under the trade name Lutensol TO5 and 8 g of DI water. The cup was spun for two 30 second cycle at maximum speed using a SpeedMixer DAC 150. The mixture was diluted with 62.3 g of water. 0.09 g of acetic acid and 2.9 g of glycerin were post added into this emulsion. The resulting emulsion had 20% of pedant aminosiloxane polymer. Particle size of the emulsion was at 24 to 78 nanometers at median diameter measured in volume mode.

Example 3: Use of Emulsion a from Example 1 for a Leave in Conditioner

A frizz control study was performed using Emulsion A prepared as described above in Example 1 and diluted to 2% active. This diluted emulsion was used as a leave in conditioner and tested for frizz control, as follows. Frizzy Type A tresses, 4 g in weight and 20 cm in length, were used for all frizz control testing. After washing with a 9% sodium lauryl sulfate solution, untreated tresses and tresses treated with 0.4 g of the diluted Emulsion A were allowed to air dry overnight at 50% relative humidity and 23° C. The tresses were then placed in a humidity chamber for 3 hours at 80% relative humidity and 25° C. The results showed good frizz control and hair fiber alignment for tresses treated with diluted Emulsion A compared to untreated tresses after these high humidity conditions. Tresses treated with diluted Emulsion A also had a smooth feel and increased shine compared to the untreated tresses.

Frizz Control after Combing was measured on treated and untreated tresses. After washing with a 9% sodium lauryl sulfate solution, an untreated tress and a tress treated with 0.4 g of the diluted Emulsion A described above were allowed to air dry overnight at 50% relative humidity and 23° C. The tresses were then combed before placing them in a humidity chamber for 3 hours at 80% relative humidity and 25° C. The results showed good frizz control and hair fiber alignment after combing followed by exposure to these high humidity conditions for tresses treated with diluted Emulsion A compared to untreated tresses. It was observed the tress treated with diluted Emulsion A did not significantly change in appearance over the 3 hours in the humidity chamber.

Frizz Control after washing was measured on treated and untreated tresses. After washing with a 9% sodium lauryl sulfate solution an untreated tress and a tress treated with 0.4 g of diluted Emulsion A described above were allowed to air dry overnight at 50% relative humidity and 23° C. The tresses were then washed with a non-silicone containing commercial cleansing shampoo and allowed to dry overnight at 50% relative humidity and 23° C. The results showed the tress treated with diluted Emulsion A kept its shape better and had less frizz than the untreated tress.

Example 4: Use of Emulsion B from Example 2 and Emulsion C from Comparative Example 1 for Leave-in Conditioner A frizz control study was performed as follows. Emulsion B prepared as described above in Example 2 was compared to Comparative Emulsion C prepared as described above in Comparative Example 1 and Emulsion D (which was an emulsion of a Silicone Quaternium-16/Glycidoxy Dimethicone Crosspolymer and Undeceth-11 and Undeceth-5). Each emulsion was diluted with water to contain 2% active, and these diluted emulsions were applied to wet, frizzy hair at level of 0.1 g/g hair and air dried overnight at 50% relative humidity and 23° C. During wet application, the tresses treated with Emulsion B had a more slippery feel compared to the untreated and Comparative Emulsion C treated tresses. The tresses were then placed in the humidity chamber for 5 hours at 80% relative humidity and 25° C. The results showed good frizz control and hair fiber alignment of tresses treated with diluted Emulsion B compared to the untreated tresses and tresses treated with diluted Emulsion D and diluted Emulsion C. The aspect ratio, (Widthmax/Lengthmax), which is a common method to measure frizz, was also measured for each tress and average of three tresses per treatment are shown in Table 2. The results show a lower aspect ratio for tresses treated with diluted Emulsion B compared to the untreated, diluted Emulsion C and diluted Emulsion D treated tresses. This corresponds to less frizz for tresses treated with diluted Emulsion B.

TABLE 2

|  | Aspect Ratio |
| --- | --- |
| Untreated (control) | 0.75 |
| Diluted Emulsion C (comparative) | 0.63 |
| Diluted Emulsion D (comparative) | 0.50 |
| Diluted Emulsion B | 0.42 |

For frizzy hair types there is a preference for less volume or fullness. The tresses from the frizz control study described above were analyzed for apparent volume using the Rumba from Bossa Nova Technologies. The integral calculation was used to measure number of pixels for each tress image and the average of three tresses per treatment is shown in Table 3. The results show lower number of average pixels, which corresponds to less volume, for tresses treated with Emulsion A compared to the untreated tresses and tresses treated with Comparative Emulsion C.

TABLE 3

|  | Number of Pixels |
| --- | --- |
| Untreated | 840252 |
| Diluted Emulsion C (comparative) | 620229 |
| Diluted Emulsion D (control) | 530611 |
| Diluted Emulsion B | 467314 |

The treatment of damaged hair with a silicone-containing conditioner can provide a protective film on the surface of the hair fibers to increase the hydrophobicity compared to untreated, damaged hair, which is more hydrophilic. Maintaining the hydrophobicity that can last through washing is a desired performance benefit. A hydrophobicity study was performed as follows. Emulsions A and D prepared as described above were used to measure hydrophobicity as follows. To measure hydrophobicity Emulsion A and Emulsion D were diluted to 3% active, applied to wet, bleached Caucasian hair and air dried overnight. The contact angle was measured using a goniometer after applying a 3 μl water droplet to the hair tress. The results in Table 4 show higher contact angle for tresses treated with Emulsion A compared to the untreated tresses and tresses treated with Emulsion D.

TABLE 4

|  | Contact Angle on Hair (°) |
| --- | --- |
| Untreated (control) | 78 |
| Diluted Emulsion D (comparative) | 114 |
| Diluted Emulsion A | 120 |

A long lasting hydrophobicity study was performed as follows. The tresses from the hydrophobicity test were then washed 15 times with a 9% sodium lauryl sulfate solution. Water contact angles were measured after specified number of washes. The results in Table 5 show a high contact angle is maintained over 15 washes for tresses treated with diluted Emulsion A and those treated with diluted Emulsion D. The untreated tresses had low contact angle before washing and even lower contact angle after 15 washes.

TABLE 5

|  | wash 0 | wash 1 | wash 3 | wash 6 | wash 10 | wash 15 |
| --- | --- | --- | --- | --- | --- | --- |
| Untreated (control) | 69 | 66 | 70 | 64 | 54 | 50 |
| Diluted Emulsion D (comparative) | 108 | 112 | 114 | 107 | 110 | 109 |
| Diluted Emulsion A | 119 | 113 | 109 | 107 | 109 | 111 |

Curl retention is an industry recognized test for determining hair styling and hold properties by subjecting curled hair tresses to constant temperature and humidity conditions for a specified period of time. Curl retention is measured by recording the difference in length of curled hair tresses before and during high humidity and constant temperature conditions. A curl retention study was performed as follows. Natural brown Caucasian hair tresses, weighing 2 g and measuring 25 cm long were used for this test. First, the tresses are pre-washed using 0.8 ml of 9% sodium lauryl sulfate solution and then dried overnight. Each tress is then wet with water and treated with 0.2 ml of a silicone emulsion diluted with water to 2% active. Then each tress was curled around a ¼" spiral perm rod and dried in an oven at 40° C. overnight. The tresses were removed from rod, keeping the curl intact and hung in a humidity. The conditions of the humidity chamber were 25° C. and 80% relative humidity. The tress lengths were then measured over 5 hour time period. Following the test, the maximum tress length was measured by uncurling it completely. The percent curl retention was calculated. An average of three tresses were measured for each treatment.

The curl retention results in Table 6 showed better curl retention for the tresses treated with diluted Emulsion B compared to the untreated tresses and similar performance to the tresses treated with diluted Emulsion D. The tresses treated with diluted Emulsion B also had tighter curl and better curl definition compared to the untreated tresses and tresses treated with diluted Emulsion D. Therefore, the Crosslinked Aminosilicone Polymer and emulsion thereof in the present invention demonstrated good styling and hold properties under the high humidity conditions tested as described herein.

TABLE 6

| | Curl Retention after 5 hours % |
|---|---|
| Untreated (control) | 36 |
| Diluted Emulsion D (comparative) | 44 |
| Diluted Emulsion B | 50 |

Example 5: Use of Emulsions, a, B, and D in Rinse-Off Conditioner

Rinse-off conditioner samples were prepared according to the following general procedure. Deionized water was added to a mixing vessel and heated to 70° C. With moderate agitation, hydroxyethyl cellulose was dispersed until fully dissolved. Heat was decreased to 60° C. and cetearyl alcohol and PEG-100 stearate and glyceryl stearate were added. The conditioner was mixed for 3 minutes and then tetrasodium EDTA was added and mixed for 3 minutes. When temperature was below 40° C., the silicone emulsion and phenoxyethanol and methylisothiazolinone were added. The water loss was compensated for and the composition was mixed for an additional 5 minutes. The final pH of the resulting conditioners were adjusted to 5. Table 7 below shows the amount of each starting material used to prepare the rinse-off conditioner samples.

TABLE 7

| Ingredient | Control Weight % | Emulsion A Weight % | Emulsion B Weight % | Emulsion D Weight % |
|---|---|---|---|---|
| Water | q.s. | q.s. | q.s. | q.s. |
| Hydroxyethylcellulose[1] | 1.5 | 1.5 | 1.5 | 1.5 |
| Tetrasodium EDTA[2] | 0.2 | 0.2 | 0.2 | 0.2 |
| Cetearyl Alcohol[3] | 1.0 | 1.0 | 1.0 | 1.0 |
| PEG-100 Stearate & Glyceryl Stearate[4] | 1.0 | 1.0 | 1.0 | 1.0 |

TABLE 7-continued

| Ingredient | Control Weight % | Emulsion A Weight % | Emulsion B Weight % | Emulsion D Weight % |
|---|---|---|---|---|
| Silicone Emulsion[5] | 0 | 6.6 | 3.3 | 4.2-8.4 |
| Phenoxyethanol and Methylisothiazolinone[6] | 0.5 | 0.5 | 0.5 | 0.5 |

[1]CELLOSIZE™ PCG-10 available from The Dow Chemical Company
[2]VERSENE™ 220 available from The Dow Chemical Company
[3]Crodacol™ CS50 available from Croda
[4]Arlacel™ 165 available from Croda
[5]Silicone Emulsion diluted to 1% active or 2% active
[6]NEOLONE™ PE available from The Dow Chemical Company A hydrophobicity study was performed using the rinse off conditioner samples prepared as described above. To measure hydrophobicity the rinse-off conditioners containing 2% active silicone from Table 7 were applied to wet, bleached Caucasian hair and air dried overnight. The contact angle was measured using a goniometer after applying a 3 μl water droplet to the hair tress. The results in Table 8 show higher contact angle, which corresponds to higher hydrophobicity for tresses treated with Emulsion A compared to the tresses treated with the control conditioner without silicone and similar contact angle to tresses treated with Emulsion D.

TABLE 8

| | Contact Angle (°) after 0 wash | |
|---|---|---|
| | T = 0s | T = 115s |
| Control | 75 | 0 |
| Emulsion D (Comparative) | 119 | 113 |
| Emulsion A | 118 | 114 |

A long lasting hydrophobicity study was performed as follows. The tresses from the hydrophobicity study above were then washed 10 times with a 9% sodium lauryl sulfate solution. Water contact angles were measured after specified numbers of washes. The results in Table 9 showed a high contact angle/hydrophobicity was maintained over 10 washes for tresses treated with conditioners containing Emulsion A and with Emulsion D. The tresses treated with the control conditioner without silicone had a low contact angle before washing and even lower contact angle after 10 washes.

TABLE 9

| | wash 0 | wash 1 | wash 3 | wash 6 | wash 10 |
|---|---|---|---|---|---|
| Control | 75 | 69 | 59 | 55 | 46 |
| Emulsion D (comparative) | 119 | 100 | 122 | 116 | 115 |
| Emulsion A | 118 | 117 | 109 | 104 | 106 |

Studies to evaluate ease of wet and dry combing were performed as follows. Medium bleached European human hair from International Hair Importers was used for testing the conditioners. Each tress weighed 2 grams. Each tress was rinsed for 15 seconds under a stream of 40° C. tap water. Using a pipette, 0.4 grams of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® brand comb, and evaluated using INSTRON WET and INSTRON DRY COMBING procedures.

For tests involving the conditioners, hair tresses were rinsed with tap water for 30 seconds at 40° C. The test conditioner was applied to the tress in the amount of 0.8 grams, and the tress was stroked for 30 seconds. The tress was rinsed for 30 seconds under tap water at 40° C. Excess water was removed by pulling the tress through the index and middle fingers of the hand. The tresses were allowed to dry separately on a paper towel overnight at room temperature. The tresses were combed once before performing the study.

INSTRON COMBING was used for determining conditioning performance by the ease of wet combing and the ease of dry combing. The test employed an INSTRON strain gauge, which was equipped to measure the force required to comb the hair. The conditioning performance was based on the ability of the hair conditioner sample, to reduce the force required to comb the hair with the INSTRON strain gauge. The force was reported as an Average Combing Load (ACL). The lower the number of the ACL value, the better was the conditioning effect imparted by the conditioner being tested. Typically, ACL baselines were initially established using untreated tresses that were only washed with a sodium lauryl sulfate solution. The effectiveness of a treatment could then be expressed as an ACL of the treated tress or percent reduction in ACL, calculated using the relationship: (untreated hair ACL−treated hair ACL)×100 divided by the untreated hair ACL According to the INSTRON WET COMBING method, hair was first wetted by dipping it into distilled water, and then the hair was detangled by combing the tress three times. The tress was then retangled by dipping in distilled water three times. Excess water was removed by passing the tress through the index and middle fingers of the hand twice. The tress was placed on a hanger and INSTRON combed. Retangling and INSTRON combing were repeated until all data points were collected. An average combing force of three tresses was measured for each treatment.

According to the INSTRON DRY COMBING method, hair was detangled by combing the tress 3 times. Then hair was retangled by swirling the tress clockwise 3 times and swirling it counter clockwise 3 times. The tress was then placed on a hanger and INSTRON combed. Retangle and Instron combing were repeated until all data points were collected. An average combing force for three tresses was measured for each treatment.

The results of INSTRON WET COMBING using conditioners containing 1% active silicone from Table 7 were shown in Table 10. The results showed the rinse-off conditioners containing Emulsion B provided a significant improvement in the reduction in wet combing force compared to the control conditioner without silicone and are similar in performance to Emulsion D containing conditioner (comparative).

The results of INSTRON DRY COMBING using conditioners containing 1% active silicone from Table 7 are shown in Table 10. The results showed the rinse-off conditioners containing Emulsion B provided a significant improvement in the reduction in dry combing force compared to the control conditioner without silicone and were similar in performance to the Emulsion D containing conditioner.

TABLE 10

|  | % Wet Reduction | % Dry Reduction |
| --- | --- | --- |
| Control | −55 | 32 |
| Emulsion D | 96 | 80 |
| Emulsion B | 97 | 81 |

Example 6—Cleansing Conditioner

Cleansing conditioner samples were prepared according to the following general procedure using the starting materials and amounts shown in Table 11, below. The first two starting materials in Phase A were combined and mixed, and heated to 75° C. Water was added to the rest of Phase A, which was let dissolve. Next Phase B was added to Phase A with mixing. The resulting mixture was cooled to 40° C., and then Phase C was added and the resulting was mixed to form the cleansing conditioner.

TABLE 11

| Phase | Ingredient | Control Weight % | Emulsion B |
| --- | --- | --- | --- |
| A | Hydroxyethyl Cellulose[1] | 1.5 | 1.5 |
|  | Tetrasodium EDTA[2] | 0.1 | 0.1 |
|  | Water | q.s. | q.s. |
| B | Cetearyl Alcohol[3] | 2.0 | 2.0 |
|  | Stearamidopropyl Dimethylamine[4] | 1.0 | 1.0 |
| C | Silicone Emulsion[5] | 0 | 6.6 |
|  | Phenoxyethanol (and) Ethylhexylglycerin[6] | 0.5 | 0.5 |

[1]CELLOSIZE™ PCG-10 available from The Dow Chemical Company
[2]VERSENE™ 220 available from The Dow Chemical Company
[3]Crodacol™ CS50 available from Croda
[4]Incromine SD-PA-(MH) available from Croda
[5]Silicone Emulsion, 2% active
[6]NEOLONE™ PE available from The Dow Chemical Company A color protection study was performed as follows. Flat tresses of slightly bleached, Caucasian hair, dyed with a commercial permanent red colorant that were 2 g in weight were used for this study. Each tress was first wet with water, treated using 0.8 g of the cleansing conditioners from Table 11, rinsed and the process was repeated. A spectrophotometer was used to measure the influence of repeated washing on the loss of redness ($\Delta a^*$), of the hair tresses compared to untreated/unwashed tresses. Testing of each treatment was performed in triplicate and colorimeter measurements were completed after every 4 treatments. The results from Table 12 showed the tresses treated with the cleansing conditioner containing Emulsion B showed less loss in redness compared to the tresses treated with the control cleansing conditioner without the Crosslinked Aminosilicone Polymer described herein after 24 washes.

TABLE 12

|  | $\Delta a^*$ after 24 washes |
| --- | --- |
| Control | −1.5 |
| Emulsion B | −0.5 |

Example 7: Conditioning Shampoos

Samples of conditioning shampoos were prepared according to the following procedures using the starting materials shown below in Table 13. With moderate agitation, the sodium lauryl ether sulfate and water were combined. Then the polyquaternium-10 was dissolved into the solution while heating. The tetrasodium EDTA was added and mixed until dissolved. The sample was heated to 75° C. and the PEG-150 pentaerythrityl tetrastearate and cocamide MEA were added. Mixing was continued for 10 minutes. Heat was then decreased, and cocamidopropyl betaine was added. When this was completely incorporated, silicone fluid was added to this base shampoo and mixed for 5 to 10 minutes. When temperature reached 40° C., the phenoxyethanol and methylisothiazolinone were added. The water loss was compensated for, and the formulation was mixed for an additional 10 minutes. The final pH of the shampoo formulations were 5 to 6.

TABLE 13

| Starting Material | Emulsion B Weight % |
|---|---|
| Deionized Water | q.s. |
| Sodium Lauryl Ether Sulfate[1] | 30 |
| Polyquaternium-10[2] | 0.3 |
| Tetrasodium EDTA[3] | 0.2 |
| PEG-150 Pentaerythrityl Tetrastearate[4] | 0.9 |
| Cocamide MEA[5] | 1 |
| Cocamidopropyl Betaine[6] | 7 |
| Silicone Emulsion[7] | 3.3 |
| Phenoxyethanol and Methylisothiazolinone[8] | 0.5 |

[1]Rhodapex ESC-3/A2 available from Solvay Novecare
[2]UCARE Polymer JR-30M available from Dow Chemical
[3]VERSEN 220 available Dow Chemical
[4]Crothix PA-(MH) available from Croda
[5]Incromide CMEA available from Croda
[6]Mackam C-37 available from Rhodia
[7]Silicone Emulsion, 1% active silicone level
[8]NEOLONE™ PE available from Dow Chemical Example 8: Styling Mousse A styling mousse was prepared as follows using the starting materials in amounts shown below in Table 14. The first two starting materials were mixed and heated to 65° C. Cocamide MEA was added. This mixture was cooled to room temperature while mixing. The acrylates copolymer was then added. The silicone emulsion was then added, followed by phenoxyethanol and methylisothiazolinone. Mixing was continued for an additional 15 minutes.

TABLE 14

| Ingredient | Emulsion B Weight % |
|---|---|
| Water | 88.4 |
| PPG-26-Buteth-26 (and) PEG-40 Hydrogenated Castor Oil[1] | 2 |
| Cocamide MEA[2] | 2 |
| Silicone Emulsion[3] | 8.2 |
| Cocamidopropyl Betaine[4] | 2 |
| PEG-12 Dimethicone[5] | 1 |
| Phenoxyethanol and Methylisothiazolinone[6] | 0.4 |

[1]Solubilisant LRI available from Sensient Cosmetic Technologies
[2]Incromide CMEA-PW-(AP) available from Croda
[3]Silicone Emulsion, 1% active silicone level
[4]Mackam C-37 available from Rhodia
[5]XIAMETER® OFX-0193 FLUID available from Dow Corning Corporation
[6]NEOLONE™ PE available from Dow Chemical Example 9—Preparation of Crosslinked Aminosilicone Polymers

TABLE 15

SAMPLE DESCRIPTION

| EXAMPLE | SAMPLE | SI ACTIVE % | PS D50 (NM) | PH |
|---|---|---|---|---|
| Comparative example | Dow Corning® CE-7080 | | | |
| X | 8566 + Gly + MA | 25 | 13.88 | 8 |
| Y | 8566 + Gly + silane(H) | 30 | 17.07 | 7-7.5 |
| Z | 8566 + Gly + silane + Maleic acid | 30 | 49 | 6-6.5 |

Example 10—SOFTNESS PANEL TESTING

Fabrics Pre-Conditioning

This step was performed to remove silicone treatment made during manufacturing of fabrics and to be sure that loads were free of silicone before our specific treatment.

Load was made with 5 new pillowcases and 4 little terry towels (30×50 cm)=1.0 kg. This load was washed 4 times in the following conditions:

Prewash 1: Miele W934—long program—water hardness: 0° F.—20 g Dash powder—Temperature: 95° C.—Spin rate: 600 rpm;

Blank 1: Miele W934—long program—water hardness: 0° F.—No detergent—Temperature: 95° C.—Spin rate: 600 rpm Prewash 2: same conditions that in prewash 1

Blank 2: same conditions as blank 1

Complete cycle of pre-conditioning was always made in the same type of washing machine (W377, W934 or W715). In order to save some time, 3 loads could be pre-washed at the same time in the same washing machine. The total load is then 3.0 kg and the quantity of detergent powder was adjusted at 60 g.

Washing Conditions: Fabric Conditioning a. Miele W377
b. Load: 5 pillow cases and 4 little terry towels (30×50 cm)=1 kg
c. Water hardness: 0° fT
d. Temperature: 40° C.
e. Spin rate: 600 RPM
f. Detergent: DASH 10 g
g. Fabric Softener: prototype fabric softener Fabric softener: a dispersion of esterquat L1/90 at 16% in water, to which was added the amount of emulsion containing the Crosslinkes Aminosilicone Polymer prepared in Example 9 or comparative system at the level of active indicated in Table 16, were prepared under mixing using a magnetic stirrer during 5 min, 24 h before the test.

6 g of prepared fabric softening composition were then placed in the softener compartment of the washing machine, which dispensed the composition automatically at the last rinse.

Little terry towels were line dried overnight before being used for panel test.

Washing machines were cleaned after treatment by performing awash cycle at 95° C. without load. In case of treatment with softener, softener drawer was manually cleaned with water before cleaning wash cycle.

Panel Test

This test was performed to determine the Softness of dry fabrics after wash cycle. One terry towel was used for 4 panelists and after was replaced by another one. Two towels were compared. The following questions were asked to 16 panelists:

a. "Which towel is the softest?"
b. "If the first fabric is the reference and quoted 5 on a scale of 1 to 10 how would you rate (the) other(s), considering 10 means very soft, smooth?"

In Table below, the results of the pair comparison are presented. Of 16 panelists, 12, 15 and 15 panelists selected respectively a terry towel treated with sample of Example X, Y and Z as softer than the reference without silicone. Their quotation was also larger than 5 respectively 5.78, 6.03 and 6.38 for samples in example X, Y & Z. This demonstrated the benefits of this technology in delivering softness on fabric from a fabric softener.

TABLE 16

|  | Average Quotation | Number of panelist/16 |
| --- | --- | --- |
| KaO + 2% Example X | 5.78 | 12 |
| KaO + 2% Example Y | 6.03 | 15 |
| KaO + 2% Example Z | 6.38 | 15 |

A-XRF Evaluation

Model Wash Protocol for Silicone Deposition Evaluation

A model protocol to mimic wash protocol is described here below.

Fabrics Pre-Conditioning

This step was performed to remove silicone treatment made during manufacturing of fabrics and to be sure that loads were free of silicone before treatment with the Crosslinked Aminosilicone Polymer prepared in Example 9.

Small pieces of knitted cotton fabric (50 g) were used as loads for this experiment. 3 kg of these small knitted cotton fabrics were pre-washed in an Electrolux type of washing machine following the procedure below:

3 kg knitted cotton fabrics in washing machine
add 40 g of powder
Run 1 cycle at 90° C., 1400 RPM
Run 6 cumulative "blank cycle" at 90° C., 1400 RPM.

Wash Step:

In a 2 L beaker, the following were added:
1. 1 L of water (hardness 16dH, temperature 40° C.)
2. silicone emulsion and disperse (2% Crosslinked Aminosilicone Polymer, based on the quantity of liquid detergent)
3. liquid detergent and disperse (5 g)
4. Add Fabrics (4 little pieces of cotton fabrics—knitted cotton—50 g)
5. Soak time without any stirring: 3 min
6. wash: 5 min, stirring is made with a spatula, "hand stirring"
7. Wring: fabrics+water weight—150 g transferred Rinse Step In a 2 L beaker, the following were added:
8. 1 L of water (hardness 16 dH, temperature 40° C.)
9. Rinse: 3 min, stirring is made with a spatula, "hand stirring"
10. Fabrics are removed with/without drainage and hung during 2-3 hours
11. XRF cups preparation (fabrics are still a bit moist)
12. Dry 48 h before XRF measurement In Case A, step 1 to 12 were applied to the fabric but not steps 8 and 9: No rinse was applied, fabrics were hung without drainage In Case B, step 1 to 12 were applied to the fabric corresponding to a full washing cycle.

XRF Method

The determination of total silicon has become important to predict silicone deposition onto surface of cotton fabric specimens. X-ray fluorescence spectrometry appeared to be one suitable technique capable of producing rapid and reproducible silicon analyses with minimal sample preparation. The comparison of silicon fluorescence intensity (K$\alpha$-line) from treated fabric specimens was performed by a PANalytical Axios 2.4 kW sequential Wavelength Dispersive X-ray Fluorescence (WDXRF) spectrometer, with Rhend window tube (75 µm Be end-window), power settings of 24 kV and 100 mA, curved InSb111-c crystal (special monochromator for ultra high sensitivity and improved resolution of Si), 700 µm primary collimator, beam filter 150 µm Beryllium, gas flow detector and 120 seconds irradiation time. A sample spinner was used to rotate the sample during the analysis and helped to minimize the effects of inhomogeneity in the sample. The same base fabric (same composition, weaving & thickness) was used for all samples and a blank without any coat was also measured. The spectrometer operated in helium analysis medium (20 sec medium flush time). Net fluorescence intensities of the Si K$\alpha$-line was related to the amount of silicone polymers deposited onto fabric specimens by comparing signals obtained from treated and untreated samples. The direct comparison method is preferable for partial analyses, like for the determination of one or two elements (Si and S) in a matrix assumed constant for all specimens to analyze.

All fabric material were cut to square-shaped specimens to fit into standard 40 mm diameter size XRF cups and used to close the cup instead of the thin-film sample support. The fabric sample was initially grasped and held taut at all points of contact by the bead and was temporally stretched until the bead finally locks in the cell neck. If the fabric support was positioned properly it should have been wrinkle-free and taut. During the preparation of the XRF cups, it was primordial to prevent the fabric sample from contacting the surface preparation area and introducing contamination of the fabric surface. For each sample, four specimens were prepared in XRF cups to have an idea of the homogeneity of silicon deposition.

As shown table 17, below, when no silicone is placed in the beaker a residual signal is measured corresponding to residual silicone treatment on fabrics.

Example X, Y and Z show silicone deposition during the wash as well as comparative example. However, in example Y and Z, the residual silicone after full cycle, meaning after the rinse is higher than in the comparative example. This demonstrates the ability of the present invention to provide higher substantivity on fabrics despite the rinse phase.

Example 11—Preparation of Emulsion E

Into a glass bottle was weighted 98 g of Crosslinked Aminosiloxane Emulsion A, followed by 2 g of Maleic Acid aqueous solution (20 wt %). The mixture was kept at 70° C. with mixing at 200 rpm. Particle size of emulsion was at 49-78 nanometer at median diameter measured in volume mode. This was referred to as Emulsion E. Emulsion E was tested as described above. The results are in Tables 15-17 below.

TABLE 15

| Example | Sample | Si Active % | PS D50 (nm) | pH |
|---|---|---|---|---|
| Comparative Emulsion D | described in Comparative Example 1 | 22 | 60 | 7.5-8 |
| Emulsion A | Aminosiloxane + Glycidol + epoxy trimethoxysilane as described in Example 1 | 30 | 17.07 | 7-7.5 |
| Emulsion E | Aminosiloxane + Glycidol + epoxy trimethoxysilane+ Maleic acid | 30 | 49 | 6-6.5 |

TABLE 16

| | Average Quotation | Number of panelist/16 |
|---|---|---|
| KaO + 2% Emulsion A | 6.03 | 15 |
| KaO + 2% Emulsion E | 6.38 | 15 |

TABLE 17

| | Si Signal (Kcps) | | | |
|---|---|---|---|---|
| Sample | Case A- no Rinse | RSD (%) | Case B- Complete Cycle | RSD (%) |
| No silicone | 0.241 | 0.14 | 0.34 | 0.45 |
| Emulsion A | 1.407 | 0.2 | 0.934 | 0.09 |
| Emulsion E | 1.499 | 0.11 | 0.716 | 0.09 |
| Comparative Emulsion D | 2.111 | 0.18 | 0.329 | 0.18 |

INDUSTRIAL APPLICABILITY

Without wishing to be bound by theory, it is thought that the present invention may provide a cost effective Crosslinked Aminosilicone Polymer. Without wishing to be bound by theory, it is thought that the Crosslinked Aminosilicone Polymer may provide one or more benefits in hair care compositions, e.g., conditioning benefits, including wet and dry combing; smooth feeling; styling benefits such as curl retention, hair alignment, or frizz reduction; color protection for colored hair; or improved hydrophobicity.

Definitions and Usage of Terms

All amounts, ratios, and percentages are by weight unless otherwise indicated. The articles 'a', 'an', and 'the' each refer to one or more, unless otherwise indicated. The disclosure of ranges includes the range itself and also anything subsumed therein, as well as endpoints. For example, disclosure of a range of 2.0 to 4.0 includes not only the range of 2.0 to 4.0, but also 2.1, 2.3, 3.4, 3.5, and 4.0 individually, as well as any other number subsumed in the range. Furthermore, disclosure of a range of, for example, 2.0 to 4.0 includes the subsets of, for example, 2.1 to 3.5, 2.3 to 3.4, 2.6 to 3.7, and 3.8 to 4.0, as well as any other subset subsumed in the range. Similarly, the disclosure of Markush groups includes the entire group and also any individual members and subgroups subsumed therein. For example, disclosure of the Markush group a hydrogen atom, an alkyl group, an aryl group, or an aralkyl group includes the member alkyl individually; the subgroup alkyl and aryl; and any other individual member and subgroup subsumed therein.

Abbreviations used herein are defined as follows. The abbreviation "$cm^2$" means square centimeters. The abbreviation "cP" means centiPoise. "DP" means the degree of polymerization. "FT-IR" means Fourier Transfer Infrared. The abbreviation "g" means grams. "GPC" means gel permeation chromatography. The abbreviation "hr" means hours. "L" means liter. The abbreviation "mg" means milligrams. The abbreviation "mm" means millimeters. "Mn" means number average molecular weight. Mn may be measured using GPC. The abbreviation "mPa·s" means milliPascal seconds. "Mw" means weight average molecular weight. "NMR" means nuclear magnetic resonance. The abbreviation "ppm" means parts per million. The abbreviation "rpm" means revolutions per minute. "RT" means room temperature of 25° C.

"Alkyl" means an acyclic, branched or unbranched, saturated monovalent hydrocarbon group. Examples of alkyl groups include methyl, ethyl, propyl (including n-propyl and iso-propyl), butyl (including n-butyl, iso-butyl, sec-butyl, and tert-butyl), pentyl, hexyl; and as well as other branched saturated monovalent hydrocarbon groups with 5 or more carbon atoms. Alkyl groups have at least one carbon atom. Alternatively, alkyl groups may have 1 to 12 carbon atoms, alternatively 1 to 10 carbon atoms, alternatively 1 to 6 carbon atoms, alternatively 1 to 4 carbon atoms, alternatively 1 to 2 carbon atoms, and alternatively 1 carbon atom.

"Alkenyl" means an acyclic, branched, or unbranched monovalent hydrocarbon group, where the monovalent hydrocarbon group has a double bond. Alkenyl groups include ethenyl, allyl, and hexenyl, including branched and linear isomers. Alkenyl groups have at least 2 carbon atoms. Alternatively, alkenyl groups may have 2 to 12 carbon atoms, alternatively 2 to 10 carbon atoms, alternatively 2 to 6 carbon atoms, alternatively 2 to 4 carbon atoms, and alternatively 2 carbon atoms.

"Alkynyl" means an acyclic, branched, or unbranched monovalent hydrocarbon group, where the monovalent hydrocarbon group has a triple bond. Alkynyl groups include ethynyl and propynyl. Alkynyl groups have at least 2 carbon atoms. Alternatively, alkynyl groups may have 2 to 12 carbon atoms, alternatively 2 to 10 carbon atoms, alternatively 2 to 6 carbon atoms, alternatively 2 to 4 carbon atoms, and alternatively 2 carbon atoms.

"Aryl" means a hydrocarbon group derived from an arene by removal of a hydrogen atom from a ring carbon atom, which may or may not include pendant groups. Aryl is exemplified by, but not limited to, phenyl and naphthyl, tolyl, xylyl, phenyl ethyl, phenyl propyl, phenyl butyl and benzyl. Aryl groups have at least 5 carbon atoms. Monocyclic aryl groups may have 5 to 12 carbon atoms, alternatively 6 to 12 carbon atoms, and alternatively 6 carbon atoms. Polycyclic aryl groups may have 10 to 17 carbon atoms, alternatively 10 to 14 carbon atoms, and alternatively 12 to 14 carbon atoms.

"Divalent hydrocarbon group" includes alkylene groups such as methylene, ethylene, propylene (including isopropylene and n-propylene), and butylene (including n-butylene, t-butylene and isobutylene); and pentylene, hexylene, heptylene, octylene, and branched and linear isomers thereof; arylene groups such as phenylene, e.g., orthophenylene; and alkaralkylene groups such as:

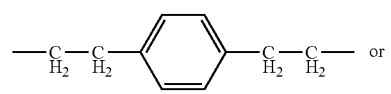 or

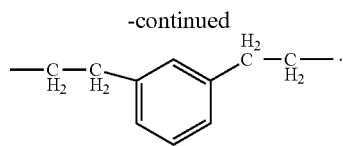

Alternatively, each divalent hydrocarbon group may be ethylene, propylene, butylene or hexylene. Alternatively, each divalent hydrocarbon group may be ethylene or propylene.

The invention claimed is:

1. A crosslinked aminosilicone polymer comprising average unit formula:

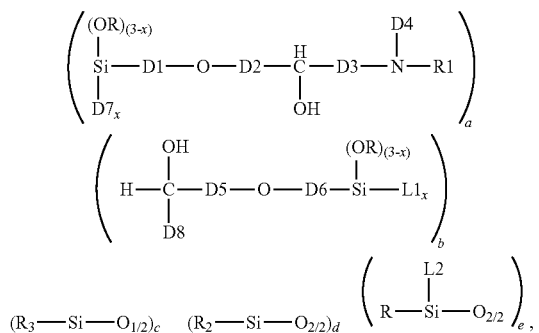

where
each R is an independently selected monovalent hydrocarbon group of 1 to 6 carbon atoms;
each L1 is an independently selected linking moiety, where L1 bonds with D7;
each L2 is an independently selected linking moiety, where L2 bonds with D4;
each D1 is an independently selected divalent hydrocarbon group of 2 or more carbon atoms;
each D2 is an independently selected divalent hydrocarbon group of 1 or more carbon atoms;
each D3 is independently selected from a covalent bond or a divalent hydrocarbon group of 1 or more carbon atoms;
each D4 is an independently selected divalent hydrocarbon group of 2 or more carbon atoms, an aminofunctional alkylene group of 2 or more carbon atoms, or a group which is a reaction product of NH reacting with an epoxy functionality;
each R1 is independently a hydrogen atom or a covalent bond linking to D8;
each D5 is an independently selected divalent hydrocarbon group of 1 or more carbon atoms;
each D6 is an independently selected a divalent hydrocarbon group of 2 or more carbon atoms;
D7 is an oxygen atom when subscript x>0, and D7 is absent when x=0;
each subscript x is independently 0, 1, or 2;
each D8 is a divalent hydrocarbon group of 1 or more carbon atoms;
subscript a is 1 or more;
subscript b is 1 or more;
subscript c is 2 or more;
subscript d is 0 or more;
subscript e is 0 or more;

a quantity (c+d+e) is up to 2000; with the proviso that subscripts a and b and group D4 are selected such that the crosslinked aminosilicone polymer has >0 to 10% amine content.

2. The polymer of claim 1, where (i) subscript a is 1 to 100; (ii) subscript b is 1 to 100, (iii) subscript c is 2 to 100, (iv) subscript d is 0 to 2,000, (v) subscripts a and b are group D4 are selected such that the crosslinked aminosilicone polymer has >0 to 5 mole % amine content; (vi) each D8 is a covalent bond or methylene; (vii) each D6 has 2 to 4 carbon atoms; (viii) each D5 has 1 to 3 carbon atoms; (ix) each D2 has 2 to 8 carbon atoms; (x) each D1 has 2 to 4 carbon atoms; (xi) each R is an alkyl group; or (xii) two or more of (i) to (xi).

3. A process for preparing the polymer of claim 1, where the process comprises
emulsion polymerization of starting materials comprising:
(i) an epoxy-functional organic compound having an alcohol functionality, (ii) an organosilicone polymer having a nitrogen containing monovalent hydrocarbon, (iii) an organosilane having an alkoxy group and an epoxy-functional group, (iv) a surfactant, and (v) water.

4. The process of claim 3, where starting material (i) is selected from the group consisting of glycidol methacrylate; n-butyl glycidyl ether; phenyl glycidol ether; 3,4-epoxy-1-cyclohexene; 9-OXABICYCLO[6.1.0]NON-2-ENE; 1-METHYL-7-OXABICYCLO[4.1.0]HEPT-3-ENE; metoprolol hydroxy epoxide; 1,2-epoxy-9-decene; and glycidol.

5. The process of claim 3, where starting material (ii) has average formula: $(R_3SiO_{1/2})_c(R_2SiO_{2/2})_d(RR4SiO_{2/2})_e$, where R4 is an aminofunctional group of formula:

where D12 is a divalent hydrocarbon group of 1 to 8 carbon atoms, and D13 is a divalent hydrocarbon group of at least 1 carbon atom.

6. The process of claim 3, where starting material (iii) has formula:
$R^ESiR_{(3-x)}(OR)_x$, where subscript x is 1 to 3, each R is independently a monovalent hydrocarbon group of 1 to 12 carbon atoms, and each $R^E$ is an epoxy-functional monovalent group.

7. A method for treating a fiber or textile comprising:
(A) applying to the fiber or textile, a treatment composition comprising the Crosslinked Aminosilicone Polymer of claim 1, and
optionally (B) drying the textile.

8. A personal care composition comprising:
(1) the Crosslinked Aminosilicone Polymer of claim 1, and
(2) a carrier that permits application.

9. A shampoo comprising:
(1) the Crosslinked Aminosilicone Polymer of claim 1,
(2) water, and
(3) an anionic surfactant and/or an amphoteric surfactant,
optionally (4) a preservative, and
optionally (5) a cationic deposition polymer, and
optionally (6) a thickener.

10. A hair conditioner comprising:
(A) the Crosslinked Aminosilicone Polymer of claim 1,
(B) water,
optionally (C) a thickener,
(D) a fatty alcohol,
optionally (E) other emulsifiers,
optionally (F) a preservative, and
optionally (G) a cationic surfactant.

11. An anhydrous leave in hair treatment composition comprising:
 (A) the Crosslinked Aminosilicone Polymer of claim 1, and
 (B) an organic or silicone carrier.

12. A styling aid comprising:
(A) the Crosslinked Aminosilicone Polymer of claim 1, and
 (B) water,
 optionally (C) a thickener,
 optionally (D) an additional emulsifier,
 optionally (E) a cationic polymer,
 optionally (F) an organic styling polymer, and
 optionally (G) a preservative.

13. A fabric softener comprising:
 (A) the Crosslinked Aminosilicone Polymer of claim 1,
 (B) water,
 (C) a fragrance,
 (D) a cationic surfactant, and
 optionally (E) a thickener.

14. An emulsion comprising:
 (1) the Crosslinked Aminosilicone Polymer of claim 1,
 (2) a surfactant, and
 (3) water.

15. A method for treating a fiber or textile comprising:
 (A) applying to the fiber or textile, a treatment composition comprising the emulsion of claim 14, and
 optionally (B) drying the textile.

16. A personal care composition comprising:
 (1) the emulsion of claim 14, and
 (2) a carrier that permits application.

17. A shampoo comprising:
 (1) the emulsion of claim 14,
 (2) water, and
 (3) an anionic surfactant and/or an amphoteric surfactant,
 optionally (4) a preservative, and
 optionally (5) a cationic deposition polymer, and
 optionally (6) a thickener.

18. A hair conditioner comprising:
 (A) the emulsion of claim 14,
 (B) water,
 optionally (C) a thickener,
 (D) a fatty alcohol,
 optionally (E) other emulsifiers,
 optionally (F) a preservative, and
 optionally (G) a cationic surfactant.

19. A styling aid comprising:
 (A) the emulsion of claim 14, and
 (B) water,
 optionally (C) a thickener,
 optionally (D) an additional emulsifier,
 optionally (E) a cationic polymer,
 optionally (F) an organic styling polymer, and
 optionally (G) a preservative.

20. A fabric softener comprising:
 (A) the emulsion of claim 14,
 (B) water,
 (C) a fragrance,
 (D) a cationic surfactant, and
 optionally (E) a thickener.

* * * * *